United States Patent [19]

Schwab et al.

[11] Patent Number: 5,273,989
[45] Date of Patent: Dec. 28, 1993

[54] 3,5-DISUBSTITUTED 2-ISOXAZOLINES AND ISOXAZOLES, AGENTS CONTAINING THEM AND THEIR USE

[75] Inventors: Wilfried Schwab; Hiristo Anagnostopulos; Elena Porsche-Wiebking; John Grome, all of Wiesbaden, Fed. Rep. of Germany

[73] Assignee: Hoechst Aktiengesellschaft, Frankfurt am Main, Fed. Rep. of Germany

[21] Appl. No.: 683,068

[22] Filed: Apr. 10, 1991

[30] Foreign Application Priority Data

Apr. 12, 1990 [DE] Fed. Rep. of Germany ....... 4011880

[51] Int. Cl.⁵ .................... A61K 31/42; C07D 413/02; C07D 401/02; C07D 261/12
[52] U.S. Cl. ................................ 514/378; 514/236.8; 514/326; 514/340; 544/137; 546/22; 546/208; 546/275; 548/119; 548/240; 548/243; 548/244; 548/247; 548/248
[58] Field of Search ............... 548/243, 244, 119, 240, 548/247, 248; 546/275, 208, 22; 544/137; 514/236.8, 326, 340, 378

[56] References Cited

U.S. PATENT DOCUMENTS

| 3,152,139 | 10/1964 | Leonard et al. ...................... 548/244 |
| 4,764,522 | 8/1988 | Imhof et al. ......................... 514/354 |
| 4,985,428 | 1/1991 | Carenzi et al. ...................... 514/352 |
| 5,006,515 | 4/1991 | Schwab et al. ....................... 514/89 |
| 5,064,847 | 11/1911 | Hubl et al. ......................... 548/243 |

FOREIGN PATENT DOCUMENTS

| 24195/88 | 4/1989 | Australia . |
| 826165 | 10/1969 | Canada ................. 548/243 |
| 0313997 | 5/1989 | European Pat. Off. . |
| 3736113 | 5/1989 | Fed. Rep. of Germany . |
| 74374 | 3/1991 | Japan ..................... 548/243 |
| 443301 | 9/1967 | Netherlands .......... 548/243 |
| 1146448 | 3/1969 | United Kingdom ............... 548/243 |
| 2163746 | 3/1986 | United Kingdom . |
| 8401774 | 5/1984 | World Int. Prop. O. .......... 548/243 |
| 88/09330 | 12/1988 | World Int. Prop. O. . |

OTHER PUBLICATIONS

Christensen et al., "Decrease . . .", CA 91:32865f (1979).
Lauridsen et al., Ibotenic Acid Analogues, J. Med. Chem., vol. 28, No. 5, 1985, pp. 668–672.
DeAmici et al., Synthesis . . . Muscarone, Chem. Abstracts, vol. 112, No. 5, 1990, 35731x.
Krogsgaard-Larsen et al., Ibotenic Acid Analogues, J. Med. Chem., vol. 27, 1984, pp. 585–591.
Krogsgaard-Larsen et al., Synthesis and . . . Ibotenic Acid, J. Med. Chem., vol. 28, 1985, pp. 673–679.
W. D. Lust et al., A Role for . . . Ischemia, Metabolic Brain Disease, vol. 3, No. 4, (1988), pp. 287–292.
Thompson et al., New Naturally Occurring Amino Acids, (1969), pp. 137–158.
G. S. Skinner, Deaminization . . . Compounds, Aliphatic Diazonium Salts, (1924) pp. 731–741.
S. M. Rothman et al., Excitotoxicity and the NMDA Receptor, TINS, vol. 10, No. 7, (1987), pp. 299–302.

*Primary Examiner*—C. Warren Ivy
*Assistant Examiner*—Celia Chang
*Attorney, Agent, or Firm*—Finnegan, Henderson, Farabow, Garrett & Dunner

[57] ABSTRACT

Novel 3,5-disubstituted 2-isoxazolines and isoxazoles and novel pharmaceuticals are described which are suitable, in particular, for the prophylaxis and/or treatment of pathological, neurodegenerative disorders in humans and animals. Processes for the preparation of these 3,5-disubstituted 2-isoxazolines and isoxazolines and isoxazoles are additionally indicated.

19 Claims, No Drawings

3,5-DISUBSTITUTED 2-ISOXAZOLINES AND ISOXAZOLES, AGENTS CONTAINING THEM AND THEIR USE

DESCRIPTION

The present invention relates to novel 3,5-disubstituted 2-isoxazolines and isoxazoles and to novel pharmaceuticals which are suitable in particular for the prophylaxis and/or treatment of pathological neurodegenerative disorders in humans and animals.

Phosphorus-containing 3,5-disubstituted 2-isoxazolines and isoxazoles are known from German Offenlegungsschrift 3,736,113 (HOE 87/F 315). Muscimol and its analogs are described, for example, in J. Med. Chem. 27 (1984), 585-591 and J. Med. Chem. 28 (1985), 668-679.

A large number of neuropathological situations are characterized by a degeneration and the loss of neurons. This applies in particular to neurodegenerative disease syndromes, such as stroke, temporary cerebral ischemia (TIA), cerebral infarct with only partially reversible symptoms (PRIND), cerebral palsy, cerebral hypoglycemia, ischemic events during cardiac arrest or surgical interventions in the heart-lung area, anoxic state, for example after drowning, intoxication or spinal cord injuries, perinatal asphyxia, age-related neurodegenerative changes, Alzheimer dementia (SDAT), pain, oversecretion of growth hormone and luteinizing hormone, schizophrenia, epilepsy, Huntington's chorea and other chronic neurodegenerative disorders.

It is furthermore known that in the mammalian brain there are numerous excitatory synaptic receptors which are activated by naturally occurring L-glutamine and L-aspartic acid. These amino acids are absorbed into the presynaptic vesicle by a high affinity transport system to complete a neuron stimulus. This transport mechanism is $Na^+$-dependent. The absorption of the amino acids L-Gln and L-Asp into the presynaptic vesicle is necessarily also dependent, inter alia on ATP to maintain the intracellular $Na^+$ concentration (Erecinska, Biochem., Pharmacol. 36 (1987), 3547-3555). An accumulation of excitatory amino acids in the synaptic gap, such as, for example, after hypoxic or ischemic conditions, can lead to continual nerve impulses, to pathological changes and finally to the irreversible degeneration of the neurons. There are indications from the literature that preparations which directly improve amino acid absorption into the synaptic vesicles reduce release, or indirectly favor back transport, and also that substances which antagonize receptor activation act neuroprotectively (Gill et al., Neuroscience, 25 (1988) 847-855; Jarvis et al., Syanpse, 2 (1988) 577-584; Kaneko et al., Arzneimittel-Forschung, 39 (1989) 445-450; Silverstein et al., J. Neurochem., 47 (1986) 1614-1619; Weiss et al., Brain Res., 380 (1986) 186-190).

Other amino acids such as, for example, N-methyl-D-aspartic acid (NMDA), kainic acid and quisqualic acid are also known as potent excitatory neurotransmitters in the central nervous system. They were used for the characterization of the glutamate receptor subtypes. These excitatory receptors, localized on the so-called glutamatergic neurons, are classified in two groups; NMDA and non-NMDA receptors. According to the present state of knowledge, the NMDA receptors are substantially involved in neuron degeneration after ischemic events, such as, for example, stroke (Rothman et al., TINS, 10 (1987) 299-302).

The invention is therefore based on the object of finding novel, potent "glutamate antagonists" which can reduce, free from undesired side effects, the cell degeneration due to hypoxia and/or ischemia. However, clinical successes with NMDA receptor antagonists having cerebral protective activity have largely failed to materialize because of adverse effects, such as, for example, the in some cases marked motor dyscoordination, psychotic effects, and other, partly toxic side effects (Handelmann et al., Eur. J. Pharmacol., 140 (1987) 69-73; Morris et al., Nature, 319 (1986) 774-776). At present, there is no known substance on the market which is clinically tested and which has shown action in neurodegenerative disorders while having good tolerability. There is thus an urgent need for novel, chemically defined and well-tolerated substances having cerebroprotective activity, which are suitable for the phophylaxis and/or aftertreatment of the pathological conditions described above, in particular of stroke.

Surprisingly, it has now been found that by introducing certain groups, in particular derived from alkylcarboxylic acids, into the 3- or 5-position, and also optionally substituted basic groups into the 5- or 3-position of 2-isoxazolines and isoxazoles, compounds are obtained which fulfill the requirements mentioned above by virtue of their biochemical and pharmacological properties, and are accordingly suitable for the prophylaxis and/or treatment of disorders which accompany cerebral neurodegenerative changes. The compounds have excellent tolerability compared to substances known from the literature, such as, for example, muscimol [5-(aminomethyl)-3(2H)-isoxazolone], MK-801 [(+)-5-methyl-10,11-dihydro-5H-dibenzo[a,d]cyclohept-5-en-10-imine] and CCP [3-(+)-2-carboxypiperazin-4-yl-propyl-1-phosphonic acid] (Lust et al., Metabolic Brain Disease, 3 (1988) 287-292, Rod et al., Can. J. Neurol. Sci., 16 (1989) 340-344, Meldrum et al., "Pharmacology of Cerebral Ischaemia" Ed. J. Krieglstein, CRC Press, 1989, 157-163) and potent action in biochemical "in vitro" and pathological animal models which can be illustrated as exemplified by the

- stimulation of the high affinity absorption of 3H-aspartate into synaptic vesicle preparations from rat brain,
- inhibition of the release of 3H-acetylcholine from striatum sections of rats,
- inhibition of 3H-MK801 binding to membranes of rat brain,
- inhibition of NMDA-induced cramps in the mouse, neuroprotective action after bilateral occlusion of the carotid artery in the Mongolian gerbil, and reduction of the infarct volume after photochemically induced focal ischemia in the rat.

This invention thus relates to novel 3,5-disubstituted 2-isoaxolines and isoxazoles of the formulae Ia, Ib or Ic

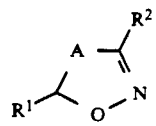

(Ia)

-continued

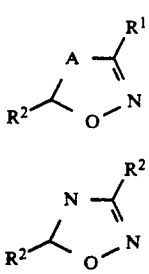
(Ib)

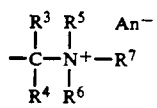
(Ic)

in which

R$^1$ is 2-, 3- or 4-pyridyl or a radical of the formula II

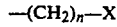
(II)

in which

R$^3$ and R$^4$ independently of one another are hydrogen or C$_1$-C$_4$-alkyl;

R$^5$ is a free electron pair of hydrogen;

R$^6$ and R$^7$ independently of one another are hydrogen; C$_1$-C$_6$-alkyl; C$_3$-C$_6$-cycloalkyl; C$_6$-C$_{12}$-aryl-C$_1$-C$_4$-alkyl; carbamimidoyl; C$_1$-C$_6$-alkylcarbonyl, C$_1$-C$_4$-alkenylcarbonyl, C$_1$-C$_6$-alkyloxycarbonyl, C$_2$-C$_{12}$-aryl-C$_1$-C$_4$-alkylcarbonyl, C$_6$-C$_{10}$-aryl-C$_1$-C$_4$-alkyl-oxycarbonyl, C$_6$-C$_{10}$-arylcarbonyl, or the radical of a naturally occurring a-amino acid or c-aminobutyric acid (Gaba) which can be substituted by C$_1$-C$_6$-alkyl, hydroxyl, halogen, amino or nitro; or R$^6$ and R$^7$, together with the nitrogen atom linking them, form a five- to seven-membered heterocycle, in which a carbon atom can be replaced by a sulfur, oxygen or nitrogen atom; or R$^5$, R$^6$ and R$^7$ independently of one another are C$_1$-C$_4$-alkyl or C$_3$-C$_6$-cycloalkyl, or R$^5$ is C$_1$-C$_4$-alkyl and R$^6$ and R$^7$, together with the nitrogen atom linking them, form a five- to seven-membered heterocycle, or R$^5$, R$^6$ and R$^7$, together with the nitrogen atom linking them, form a six- to twelve-membered bicyclic heterocycle;

An$^-$ is an anion radical of a physiologically acceptable salt, or an internal anionic radical when the compound is zwitterion R$^2$ is a radical of the formula III —(CH$_2$)$_n$—X  (III)

in which n is 0 or an integer from 1 to 4;

X is hydroxyl; C$_1$-C$_4$-alkyloxy; carboxyl; haloformyl; formyl; oxyimino; C$_1$-C$_{12}$-alkyloxycarbonyl; benzyloxycarbonyl or C$_3$-C$_6$-cycloalkyloxycarbonyl, which can be mono- substituted or polysubstituted by C$_1$-C$_6$-alkyl; or is carbonyl which is linked by a peptide bond to a naturally occurring a-amino acid, c-aminobutyric acid or a dipeptide, or is aminocarbonyl in which amino can be mono- or disubstituted by C$_1$-C$_6$-alkyl or monosubstituted by phenyl-C$_1$-C$_6$-alkyl, or both amino radicals, together with the nitrogen atom linking them, form a five- to seven-membered heterocycle in which a carbon atom can be replaced by an oxygen or nitrogen atom;

or X is a group of the formula IV

(IV)

in which

Y and Z independently of one another are hydroxyl, C$_1$-C$_4$-alkyl or C$_1$-C$_4$-alkyloxy; and A is a C,C-single or a C,C-double bond;

with the proviso that R$^1$ is not 2-, 3- or 4-pyridyl if R$^2$ is a group of the formula IV and n ]0 if X is hydroxy or methyloxy, and their optionally stereoisomeric forms and their physiologically tolerable salts.

The radical of the formula II as disclosed above:

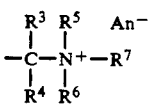
(II)

in which

R$^5$ is a free electron pair or hydrogen, can also properly be considered as being of the formulas IIa and IIb:

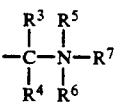
(IIa)

in which

R$^5$ is a free electron pair; and

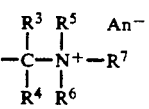
(IIb)

in which

R$^5$ is hydrogen, (C$_1$-C$_4$)-alkyl or (C$_3$-C$_6$)-cycloalkyl.

An$^-$ is an anion radical of a physiologically acceptable salt, or an internal anionic radical when the compound is a zwitterion.

If not stated otherwise in the individual case, alkyl can be straight-chain or branched. The same applies to radicals derived therefrom such as alkyloxy, alkylcarbonyl, alkyloxycarbonyl or arylalkyl.

C$_6$-C$_{12}$-aryl is preferably phenyl, naphthyl or biphenyl, in particular phenyl. Radicals derived therefrom are to be formulated accordingly, such as arylcarbonyl or arylalkyl. The term "aryl" is defined in Hackh's Chemical Dictionary, 4th Edition, 1969 and 1972, as referring to an organic radical derived from an aromatic hydrocarbon by the removal of one atom; e.g., phenyl from benzyl.

Halogen is fluorine, chlorine, bromine or iodine, preferably chlorine.

Five- to seven-membered heterocycles in the context of the present invention are, for example, pyrrole, pyridine, azepine, thiazole, isothiazole, oxazole, isoxazole, pyrazole, imidazole, thiazine, 1,2-oxazine, 1,3-oxazine, morpholine, pyridazine, pyrimidine, pyrazine, 1,2-thiazepine, 1,3-thiazepine, 1,4-thiazepine, 1,2-oxazepine, 1,3-oxazepine, 1,4-oxazepine, 1,2-diazepine, 1,3-diazepine, 1,4-diazepine and their partially or completely saturated variants. Pyrrolidine, piperidine, morpholine, piperazine or pyridine may be mentioned in particular.

Naturally occurring a-amino acids, such as, for example, Als, Arg, Cys, Gly, His, Ile, Leu, Lys, Met, Phe, Pro, Ser Thr, Trp, Tyr, Val, Asp, Asn, Glu and Gln are described, for example, in Ann. Rev. Biochem. 38 (1969) 137–158 and FEBS Letters 64 (1976) 29–35. Dipeptides in the context of the present invention contain naturally occurring a-amino acids and also c-aminobutyric acid as building blocks.

Referred compounds of the formula Ia and Ib are those in which $R^1$ is 2-, 3- or 4-pyridyl or a radical of the formula II

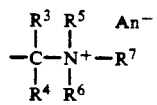
(II)

in which $R^3$ and $R^4$ independently of one another are hydrogen or $C_1$-$C_4$-alkyl;

$R^5$ is a free electron pair or hydrogen;

$R^6$ and $R^7$ independently of one another are hydrogen; $C_1$-$C_4$-alkyl; or phenyl-$C_1$-$C_2$-alkyl;

$R^6$ and $R^7$, together with the nitrogen atom linking them, form a five- to seven-membered heterocycle in which a carbon atom can be replaced by a sulfur, oxygen or nitrogen atom;

$R^6$ is hydrogen and $R^7$ is a carbamimidoyl; $C_1$-$C_6$-alkyloxycarbonyl, phenyl-$C_1$-$C_4$-alkylcarbonyl, benzyloxycarbonyl, benzoyl, or the radical of a naturally occurring a-amino acid or c-aminobutyric acid, which can be substituted by $C_1$-$C_4$-alkyl, hydroxyl, halogen, amino or nitro;

$R^5$, $R^6$ and $R^7$ independently of one another are $C_1$-$C_4$-alkyl or $C_3$-$C_6$-cycloalkyl;

$An^-$ is an anion radical of a physiologically acceptable salt, or an internal anionic radical when the compound is a zwitterion.

$R^2$ is a radical of the formula III

(III)

in which n is 0 or an integer from 1 to 3;

X is hydroxyl; $C_1$-$C_4$-alkyloxy; carboxyl; $C_1$-$C_4$-alkyloxycarbonyl; benzyloxycarbonyl or $C_3$-$C_6$-cycloalkyloxycarbonyl, which can be mono- or polysubstituted by $C_1$-$C_6$-alkyl; or is carbonyl which is linked by a peptide bond to a naturally occurring a-amino acid, c-aminobutyric acid or a dipeptide; or is aminocarbonyl in which amino can be mono- or disubstituted by $C_1$-$C_4$-alkyl or monosubstituted by phenyl-$C_1$-$C_4$-alkyl, or both amino radicals, together with the nitrogen atom linking them, form a five- to seven-membered heterocycle in which a carbon atom can be replaced by an oxygen or nitrogen atom;

or X is a group of the formula IV

(IV)

in which

Y and Z independently of one another are hydroxyl, $C_1$-$C_4$-alkyl or $C_1$-$C_4$-alkyloxy; and A is a C,C-single or a C,C-double bond; with the proviso that $R^1$ is not 2-, 3- or 4-pyridyl if $R^2$ is a group of the formula IV.

Compounds of the formula Ia may be mentioned in particular in which $R^1$ is 2-pyridyl or a radical of the formula II

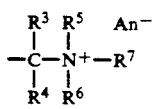
(II)

in which $R^3$ and $R^4$ independently of one another are hydrogen or $C_1$-$C_4$-alkyl;

$R^5$ is a free electron pair or hydrogen;

$R^6$ and $R^7$ independently of one another are hydrogen; $C_1$-$C_4$-alkyl; or phenyl-$C_1$-$C_2$-alkyl;

$R^6$ and $R^7$, together with the nitrogen atom linking them, form a five- or seven-membered saturated heterocycle in which a carbon atom can be replaced by a sulfur, oxygen or nitrogen atom, $R^6$ is hydrogen and $R^7$ is carbamimidoyl, $C_1$-$C_6$-alkylcarbonyl or the radical of a naturally occurring a-amino acid or c-aminobutyric acid;

$R^5$, $R^6$ and $R^7$ independently of one another are $C_1$-$C_4$-alkyl;

$An^-$ is an anion radical of a physiologically acceptable salt, or an internal anionic radical when the compound is a zwitterion.

$R^2$ is a radical of the formula III

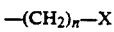
(III)

in which n is 0, 1 or 2;

X is hydroxyl; $C_1$-$C_4$-alkyloxy; carboxyl; haloformyl; $C_1$-$C_4$-alkyloxycarbonyl; benzyloxycarbonyl or $C_3$-$C_6$-cycloalkyloxycarbonyl, which can be mono- or polysubstituted by $C_1$-$C_6$-alkyl; or is carbonyl which can be linked by a peptide bond to a naturally occurring a-amino acid or c-aminobutyric acid; or is aminocarbonyl in which amino is mono- or disubstituted by $C_1$-$C_4$-alkyl, or both amino radicals, together with the nitrogen atom linking them, form a five- to seven-membered heterocycle in which a carbon atom can be replaced by an oxygen or nitrogen atom;

or X is a group of the formula IV

(IV)

in which

Y and Z independently of one another are hydroxy, $C_1$-$C_4$-alkyl or $C_1$-$C_4$-alkyloxy; and A is a C,C-single or a C,C-double bond; with the proviso that $R^1$ is not 2-pyridyl if $R^2$ is a group of the formula IV and A is not a C,C double bond if X is OH and n=0; and compounds of the formula Ia in which $R^1$ is 2-pyridyl or a radical of the formula II

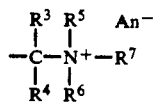 (II)

in which $R^3$ and $R^4$ independently of one another are hydrogen or $C_1$-$C_4$-alkyl;

$R^5$ is a free electron pair or hydrogen;

$R^6$ and $R^7$ independently of one another are hydrogen; $C_1$-$C_4$-alkyl; or benzyl;

$R^6$ and $R^7$, together with the nitrogen atom linking them, for a five- to six-membered saturated heterocycle, in which a carbon atom can be replaced by a sulfur, oxygen or nitrogen atom;

$R^6$ is hydrogen and $R^7$ is carbamimidoyl; $C_1$-$C_6$-alkylcarbonyl, or the radical of a naturally occurring a-amino acid;

$R^5$, $R^6$ and $R^7$ independently of one another are $C_1$-$C_4$-alkyl;

$R^2$ is a radical of the formula III

 (III)

in which n is 0, 1 or 2;

X is hydroxyl; carboxyl; $C_1$-$C_4$-alkyloxycarbonyl; benzyloxycarbonyl; cyclohexyloxycarbonyl, which can be mono- or polysubstituted by $C_1$-$C_6$-alkyl; carbonyl which is linked by a peptide bond to a naturally occurring a-amino acid; or aminocarbonyl in which both amino radicals, together with the nitrogen atom linking them, for a five- to six-membered heterocycle in which a carbon atom can be replaced by an oxygen or nitrogen atom;

or a group of the formula IV

 (IV)

in which

Y is hydroxyl or $C_1$-$C_4$-alkyloxy and

Z is $C_1$-$C_4$-alkyl; and

A is a C,C-single or a C,C-double bond; with the proviso that $R^1$ is not 2-pyridyl if $R^2$ is a group of the formula IV and A is not a C,C-double bond if X is OH and n=0.

Among the compounds of the formula Ib, those may be mentioned in particular in which $R^1$ is a radical of the formula II

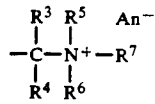 (II)

in which $R^3$ and $R^4$ are hydrogen;

$R^5$ is a free electron pair or hydrogen;

$R^6$ and $R^7$ independently of one another are hydrogen; $C_1$-$C_4$-alkyl; or phenyl-$C_1$-$C_2$-alkyl;

$R^6$ and $R^7$, together with the nitrogen atom linking them, for a five- to six-membered saturated heterocycle in which a carbon atom can be replaced by a sulfur, oxygen or nitrogen atom;

$R^6$ is hydrogen and $R^7$ is $C_1$-$C_4$-acyl; $C_1$-$C_6$-alkylcarbonyl, benzoyl or the radical of a naturally occurring a-amino acid or c-aminobutyric acid;

$R^5$, $R^6$ and $R^7$ independently of one another are $C_1$-$C_4$-alkyl or $C_3$-$C_6$-cycloalkyl;

$An^-$ is an anion radical of a physiologically acceptable salt, or an internal anionic radical when the compound is a zwitterion.

$R^2$ is a radical of the formula III

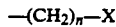 (III)

in which n is 0, 1 or 2;

X is carboxyl; haloformyl; $C_1$-$C_4$-alkyloxycarbonyl; benzyloxycarbonyl or $C_3$-$C_6$-cycloalkylcarbonyl, which can be mono- or polysubstituted by $C_1$-$C_6$-alkyl; or carbonyl which is linked by a peptide bond to a naturally occurring a-amino acid or c-aminobutyric acid; or aminocarbonyl in which amino can be mono- or disubstituted by $C_1$-$C_4$-alkyl, or both amino radicals, together with the nitrogen atom linking them, form a five- to seven-membered heterocycle in which a carbon atom can be replaced by an oxygen or nitrogen atom; and A is a C,C-single or a C,C-double bond, and compounds of the formula Ib in which $R^1$ is a radical of the formula II

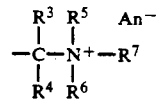 (II)

in which $R^3$ and $R^4$ are hydrogen;

$R^5$ is a free electron pair;

$R^6$ and $R^7$ independently of one another are hydrogen or $C_1$-$C_4$-alkyl;

$R^6$ and $R^7$, together with the nitrogen atom linking them, form a five- to six-membered saturated heterocycle in which a carbon atom can be replaced by a sulfur, oxygen or nitrogen atom;

$R^6$ is hydrogen and $R^7$ is $C_1$-$C_6$-alkylcarbonyl;

$R^5$, $R^6$ and $R^7$ independently of one another are $C_1$-$C_4$-alkyl;

$An^-$ is an anion radical of a physiologically acceptable salt, or an internal anionic radical when the compound is a zwitterion.

$R^2$ is a radical of the formula III

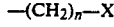 (III)

in which n is 2 and

X is carboxyl, $C_1$-$C_4$-alkyloxycarbonyl; benzyloxycarbonyl; cyclohexylcarbonyl which can be mono- or polysubstituted by $C_1$-$C_6$-alkyl; carbonyl which is linked by a peptide bond to a naturally occurring a-amino acid; or aminocarbonyl in which both amino radicals, together with the nitrogen atom linking them, form a five- to six-membered heterocycle in which a carbon atom can be replaced by an oxygen or nitrogen atom; and A is a C,C-single or a C,C-double bond.

Generally preferred compounds of the formula Ia are those in which A is a C,C-double bond.

The following may also be mentioned in particular:

benzyl 5-aminomethylisoxazole-3-propionate hydrochloride, ethyl 5-aminomethylisoxazole-3-propionate hydrochloride, (+)-menthyl 5-aminomethylisoxazole-3-propionate toluene-4-sulfonate, (−)-menthyl 5-aminomethylisoxazole-3-propionate toluene-4-sulfonate, cis-(3,3,5)trimethylcyclohexyl 5-aminomethylisoxazole-3-propionate toluene-4-sulfonate, ethyl 2-(5-aminomethylisoxazole-3-yl)ethyl-2-(P-methyl)phosphinic acid hydrochloride, methyl 5-aminomethylisoxazole-3-propionate hydrochloride, 5-aminomethylisoxazole-3-propionic acid, 5-(1-amino-1-methylethyl)isoxazole-3-propionic acid, 5-benzylaminomethylisoxazole-3-propionic acid, 5-dimethylaminomethylisoxazole-3-propionic acid, 2-(5-aminomethylisoxazole-3-yl)ethyl-2-(P-methyl)-phosphinic acid hydrochloride, 5-acetamidomethylisoxazole-3-propionic acid, (−)-menthyl 5-trimethylammoniomethylisoxazole-3-propionate iodide, (+)-menthyl 5-trimethylammoniomethylisoxazole-3-propionate iodide, (+)-menthyl 5-(L-phenylalanylamminomethyl)isoxazole-3-propionate hydrochloride, (−)-menthyl 5-(L-phenylalanylamminomethyl)isoxazole-3-propionate hydrochloride, methyl 5-(L-phenylalanylamminomethyl)isoxazole-3-propionate hydrochloride, 5-guanidinomethylisoxazole-3-propionic acid, N-(5-aminomethylisoxazole-3-yl)propionylglycine, bis(3-[2-carboxy]ethylisoxazol-5-ylmethyl)amine diammonium salt, (+)-menthyl 5-aminomethyl-2-isoxazoline-3-propionate toluene-4-sulfonate, (−)-menthyl 5-aminomethyl-2-isoxazoline-3-propionate toluene-4-sulfonate, 3-(2-carboxyethyl)-5-(2-pyridyl)-2-isoxazoline, 5-trimethylammoniomethylisoxazole-3-propionic acid ester, 5-piperidinomethylisoxazole-3-propionic acid hydrochloride, 5-aminomethylisoxazole-3-propionamide hydrochloride, 5-(L-phenylalanylamino)methylisoxazol-3-ylpropionylglycine trifluoroacetate, (−)-menthyl-3-carboxy-2-isoxazoline-5-yl-carboxylatedicyclohexylammonium salt, cis-(3,3,5)-trimethylcyclohexyl-5-trimethylammoniomethylisoxazole-3-propionate iodide, methyl-3-hydroxyliminomethyl-isoxazole-5-propionate, 3,5-dicarboxyl-2-isoxazoline, 5-hydroxylmethyl-isoxazole-3-propionate-sodium salt.

The invention furthermore relates to processes for the preparation of compounds of the formulae Ia, Ib and Ic, their possible stereoisomeric forms and, if appropriate their stereoisomeric salts, which comprises reacting a nitrile oxide of the formula V

a) in the case in which A in formula Ia is a C,C-single bond, with an olefin of the formula VI

or b) in the case in which A in formula Ia is a C,C-double bond, with a propargyl derivative of the formula VII $$CH\equiv C-\underset{R^4}{\overset{R^3}{\underset{|}{\overset{|}{C}}}}-W \qquad (VII)$$

in which $R^2$, $R^3$ and $R^4$ have the abovementioned meanings and W is a group of the formula $NR^5R^6R^7$ having the abovementioned meanings for $R^5$, $R^6$ and $R^7$, or a substituent which can be replaced by an optionally substituted amine of the formula $NR^5R^6R^7$, such as, for example, alkylsulfonyl or arylsulfonyl or halogen, preferably chlorine or bromine in this case, in a 1,3-dipolar cycloaddition, or c) converting a compound prepared according to a) or b), of the formula VIII

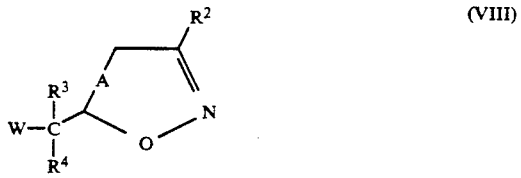

having the abovementioned meanings for $R^2$, $R^3$, $R^4$ and A by substitution of the group W with an optionally substituted amine of the formula $NR^5R^6R^7$, into a compound of the formula Ia, or d) for the preparation of a substance of the formula Ib or Ic, reacting an alkenoic or alkynoic acid derivative of the formula IX, X, XII or XIII

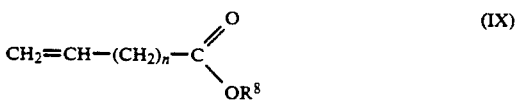

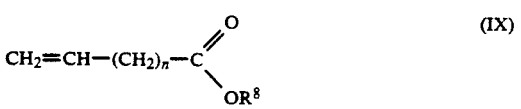

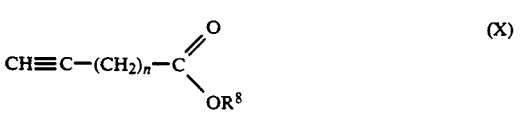

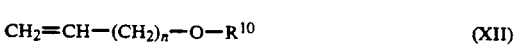

in which $R^{10}$ is hydrogen, alkyl groups, any desired protecting group for an alcohol function or an ester of a carboxylic acid, having the abovementioned meaning for n and any desired alkyl or aralkyl radical for $R^3$, with a nitrile oxide of the formula XI

$$O-N=C-R^2 \qquad (XI)$$

in which $R^2$ has the above-mentioned meaning with the proviso that $R^2$ is not a α-amino acid or a dipeptide, in a 1,3-dipolar cycloaddition, then removing the protecting group $R^{10}$ which may be present by methods known from the literature, converting the alcohol function which may be present into a derivative activated for exchange with amines such as, for example, a halide or tosylate, and then reacting this derivative with an amine of the formula $NR^5R^6R^7$ having the above-mentioned meaning for $R^5$-$R^7$ or e) hydrolyzing a carboxylic acid ester of the formula Ia or Ib prepared according to a)–d) to the carboxylic acid or hydrogenlytically cleaving a benzyl ester which may be present, or f) converting an alkyl carboxylate prepared according to methods a)–d) into the amide using an appropriately substituted primary or secondary amine, or g) hydrolyzing a monoalkyl phosphinate or dialkyl phosphonate of the formula Ia prepared according to a) or b) by methods known per se from the literature to the phosphonic acid monoester, to the phosphonic acid or to the phosphinic acid, or h) first converting a carboxylic acid obtained according to e) into an activated acid derivative, then esterifying this derivative with alcohols, converting these esters with primary and secondary amines into the amides or with optionally carboxyl-protected amino acids or lower peptides into peptides acylated on the nitrogen, and then, if desired, removing the carboxyl-protecting group on the peptide moiety or, for example, converting it into another group by transesterification, or i) in a compound of the formula Ia obtained by methods a)–h), removing a radical $R^7$ optionally used as a protecting group from the nitrogen atom by methods known from the literature, or j) converting a compound prepared according to method i), whose carboxyl group is present in esterified form or as the amide, into a derivative acylated on the nitrogen by reaction with an activated carboxylic acid derivative or, if appropriate, an amino acid protected on the nitrogen or a lower peptide using reagents customary in peptide chemistry, or k) converting a compound prepared according to method j) into a free carboxylic acid by cleavage by the carboxylic acid ester which may be present, or l) converting a compound prepared by method j) or k) into a free amino compound or a betaine by cleavable of an N-protecting group which may have been introduced with the amino acid moiety, or m) converting a compound of the formula Ia or Ib prepared by methods c)–i) into a quaternary ammonium compound by reaction with an alkylating agent, preferably an alkyl halide, or n) resolving a compound of the formulae Ia and Ib prepared according to methods a)–m), which by virtue of its chemical structure occurs in diastereoisomeric or enantiomeric forms, into the pure stereoisomers in a manner known per se, in which o) the compounds of the formulae Ia and Ib prepared by methods a)–n) are either isolated in free form or, in the case of the presence of acidic or basic groups, optionally converted into physiologically tolerable crystalline salts.

The preparation of physiologically tolerable salts is carried out in a manner known per se from compounds of the formulae Ia and Ib which are capable of salt formation, including their stereoisomeric forms. Thus, the carboxylic acids, phosphonic acids and phosphinic acids and the phosphonic acid monoesters form alkali metal salts, alkaline earth metal salts, or optionally substituted ammonium salts with basic reagents, such as hydroxides, carbonates, hydrogen carbonates, alcoholates and ammonia or organic bases, for example trimethyl- or triethylamine, ethanolamine or, alternatively, basic amino acids, for example lysine, ornithine or arginine, stable hydrogen phosphonates also being obtainable by conversion of only one of the two acidic OH groups in the case of the phosphonic acids. If the compounds of the formulae Ia and Ib have basic groups in the radical $R^1$, stable, non-toxic acid addition salts can also be prepared with strong acids. Suitable acids for this purpose are both inorganic and organic acids, such as hydrochloric hydrobromic, sulfuric, phosphoric, methanesulfonic, benzenesulfonic, p-toluenesulfonic, 4-bromobenzenesulfonic, acetic, oxalic, tartaric or trifluoroacetic acid.

Suitable counterions in the case of the quaternary ammonium salts resulting from peralkylation of amino compounds according to method m) are preferably the anions coming from the alkylating agent, such as, for example, alkyl- or arylsulfonates and also bromide and iodide, it also being possible to replace these by other physiologically tolerable anions by means of suitable ion exchangers.

The preparation and reaction of the nitrile oxides used as starting materials for 1,3-dipolar cycloadditions are described in a monograph (K.P.G. Torsell: Nitrile Oxides, Nitrones and Nitronates in Organic Synthesis, VCH Verlagsgesellschaft, Weinheim, 1988). The hydroxamoyl halides used as precursors are obtainable by methods known from the literature by halogenation of appropriate aldoximes or, in the case of chlorooximidoacetic acid esters, via a diazotiazation reaction starting from glycine alkyl esters (G. S. Skinner, J. Am. Chem. Soc. 46 (1924), 731 et seq.). Formyl oxyiminonitrile oxides were obtained by dehydrohalogenation of chlorglyoxime with triethyl amine (A. P. Kozikowski, J. Org. Chem. 48 (1983), 366). The nitro compounds also used are known from the literature in some cases or can be prepared by methods which are known in principle from the literature; thus, for example, the 4-nitrobutyric acid esters can be prepared by fluoride- or base-catalyzed addition of nitromethane to acrylic acid derivatives (S. Kanbe et al., Scient. Pap. Instit. phys. chem. Res. (Jap.) 58 (1964), 118–121; D. W. Chasar, Synthesis 1982, 841–42; N. Ono, Synthesis 1984, 226–227).

By using 1,8-diazabicyclo[5.4.0]undec-7-ene (DBU) as the base and a special reaction procedure, namely the addition of the acrylic acid ester to a 5 to 50-fold excess of nitromethane containing catalytic amounts of DBU in a temperature range from about 60° to 100° C., preferably about 70° to 90° C., the yields known from the literature can be substantially improved, and the formation of the bis-adducts normally occurring as by-products which are difficult to separate is to the greatest possible extent prevented. The addition of the ntiromethane to vinylphosphonic acid esters which is described as having yields of about 30% (T. A. Mastryukova, Izv. Akad. Nauk. SSR, Ser. Khim., 6 (1971), 1353–1354) can be substantially improved using this variant and even applied to the corresponding alkylvinylphosphinic acid esters, which corresponds to a method which was hiterto unknown from the literature. By prior reaction of acryloyl chloride with appropriately substituted alcohols using an acid scavenger, such as, for example, triethylamine, the esters of higher, cyclic, and also chiral alcohols also used here, which are in some cases unknown from the literature, are accessible without racemization, and can be advantageously used in the following synthesis steps. The optionally substituted allkyl- and propargylamine derivatives of the formulae VI and VII furthermore used as reaction components are, as fundamental substances, mostly known from the literature or even commercially available. In the case of primary or secondary amines, protecting groups known from the literature, preferably acyl or urethane protecting groups, such as, for example, acetyl, benzoyl, tert.-butoxycarbonyl, tert.-butyl or benzyloxycarbonyl are introduced before the cycloaddition, and can, it desired, be removed again by methods known from the literature after the cycloaddition. These protecting groups are preferably introduced by methods known from peptide chemistry; thus, for example, the N-tert.-butoxycarbonyl group is introduced by reaction of the appropriate amine with di-tert.butyl dicarbonate in aliphatic ethers using an amine such as, for example, triethylamine.

The production of the nitrile oxides, which easily tend to oligomerize, is advantageously carried out "in situ" in the presence of the compounds VI or VII as reaction components without intermediate isolation. When produced from nitro compounds according to Mukaiyama, aromatic isocyanate, such as, for example, phenyl isocyanates or preferably 1,4-phenylene diisocyanate or toluene-2,4-diisocyanate are preferably employed for the dehydration. In this case, it is recommended to work in an aprotic solvent or dispersing agent which is inert to the reaction components, such as, for example, ethyl acetate, dimethylformamide, dimethylacetamide, dialkyl ether, tetrahydrofuran, halogenated hydrocarbons, for example dichloromethane, chloroform or dichloroethane, hydrocarbons, such as hexane, cyclohexane, benzene, toluene or other substituted aromatics, mixtures of the above-mentioned solvents also being suitable. Organic or inorganic bases, such as, for example, tertiary amines, alkali metal carbonates or hydroxides are used to produce the nitrile oxides from hydroxamoyl halides. In this case, the reaction is carried out using organic bases, preferably in the abovementioned, optionally chlorinated aliphatic or aromatic hydrocarbons or aliphatic, including cyclic, ethers, while when using inorganic bases the reaction can also be carried out in two-phase solvent mixtures, such as, for example, ethyl acetate/water or dichloromethane/water. The preparation of the nitrile oxides and the cycloaddition are as a rule carried out at temperatures between about −20° C. and +80° C., but preferably between 0° C. and +40° C.

The reaction components in the cycloaddition are preferably employed in equimolar amounts, but in the case of a nitrile oxide which tends to oligomerize, the olefin required for scavenging can also be employed in an up to ten-fold excess. The base used for the release of the nitrile oxides from hydroxamoyl halides can also be employed in equimolar amounts or in a several-fold excess. In order to produce the nitrile oxides in a low stationary concentration, release by base or isocyanate continuously over a relatively long period, which is preferably 2 to 24 hours, is recommended. This can advantageously be carried out by slow dropwise addition of one of the reaction components required to a solution containing the remaining reagents.

The cleavage of the acyl or urethane protecting groups additionally present in the substituent $R^1$ of the formula Ia is usually carried out by methods known from peptide chemistry, where in the case of the preferably used tert.-butoxycarbonyl group, an acid cleavable, for example with alcoholic hydrochloric acid or trifluoroacetic acid, is to be preferred, while the benzyoxycarbonyl protecting group can be removed either by hydrogenolysis or by alakaline hydrolysis. The acid used for the protonolytic protecting group removal is in this case advantageously employed in a relatively large excess, while in the case where trifluoroacetic acid is used the use of the pure acid as a solvent or a mixture with a halogenated hydrocarbon, such as, for example, trichloromethane, is even recommended to accelerate the reaction. When using hydrohalic acids, an alcoholic solution, preferably a methanolic or ethanolic solution thereof, is preferably used. The acidic removal of the protecting group can be carried out in a temperature range from about 0° to +80° C. but preferably about 20° to 40° C. Suitable solvents for the hydrogenolytic cleavage of the benzyloxycarbonyl protecting group are the solvents known from the literature, such as, for example, lower alcohols or glacial acetic acid, preferably methanol. Heterogeneous catalysts, for example palladium on carbon, are preferably used as catalysts. The hydrogenation can be carried out at normal pressure or under hydrogen overpressure in a hydrogenation autoclave at temperatures from about 0° to +80° C., preferably at room temperature. The ester groups additionally present in the radical $R^2$ of the formulae Ia and Ib can be cleaved either by acid or by Base alkali, and in the case of benzyl esters also by hydrogenolysis. In the case of substituted cyclic esters, such as, for example, (+)- and (−)-menthyl esters, a mixture of trifluoroacetic acid and trifluoromethanesulfonic acid together with thioanisole has proved particularly suitable (see H. Yajima et al., Chem. Pharm. Bull. 34 (1986), 4356–4361). In the case of the tert.-butyl esters used. The conditions described above for the removal of the N-tert.-butoxycarbonyl protecting group can also be used advantageously, so that when using appropriate building blocks the protecting groups on both substituents of the heterocycle can be removed simultaneously. The alkyl esters also used are preferably subjected to alkaline hydrolysis using an equimolar to five-fold excess of alkali metal hydroxide in aqueous or aqueous-alcoholic solution. In the case of the 3-alkoxycarbonylisoxazolines and -isoxazoles, equimolar amounts of alkali metal hydroxide and temperatures from about 0° to +20° C. are sufficient owing to the activated ester group, while the ester groups bonded to the heterocycle via one or more methylene groups require more drastic conditions in the form of higher temperatures and/or greater excesses of alkali metal hydroxide. For the cleavage of the tert.-butyl or tetrahydropyranyl radicals preferably used as an alcohol protecting group, acids, such as, for example, trifluoroacetic acid or alcoholic hydrochloric acid, preferably methanolic hydrochloric acid, are preferably used. An excess of acid or, in the case of trifluoroacetic acid, the use of the pure acid as a solvent also has a positive influence on the rate of the reaction. A range from about 0° to +80° C., but preferably about 20° to 40° C., is suitable as the reaction temperature. The conversion of the phosphonic acid and phosphinic acid esters into the corresponding free acids advantageously takes place under acidic conditions, preferably in anhydrous medium; thus, for example, by using a 2- to 100-fold excess of hydrobromic acid in organic acids, such as, for example, acetic acid in a concentration of 0.5 to 4-normal, preferably 2- to 4-normal a range of about +20° to +50° C. is preferably selected for mild cleavage. To prepare the phosphonic acid half esters from phosphonic acid diesters, and also phosphinic acids from phosphinic acid esters, the appropriate esters are as a rule subjected to alkaline hydrolysis, preferably in an aqueous medium. In this case, a water-miscible lower alcohol is advantageously used to dissolve the diester and a 1- to 5-normal aqueous base, for example sodium hydroxide, is then added. The base can be used in stoichiometric amounts or in an up to 10-fold excess, preferably in an about 2- to 4-fold excess, in a temperature range from about 0° to +50° C., in particular from about 20° to 40° C.

By advantageous combination of the esters for the nitrile oxide moiety and urethane or acyl protecting groups for the amine moiety, heterocycles of the formulae Ia and Ib can be prepared whose functional acid and base group can be released together or separately by the use of alkaline, acidic or hydrogenolytic methods, some of which are described above. For the substitution of a replaceable substituent W of the formula VIII, which here is preferably a halogen atom, the reaction is carried out with a secondary amine, preferably used in an about 2 to 50-fold excess. Suitable solvents are those indicated above for carrying out the cycloaddition, and in the case of amines present in liquid form also the amine itself. The reaction temperature can be from 0° C. up to the boiling temperature of the solvent used, preferably about 0° C.–+50° C. When using volatile or gaseous amines, the reaction is advantageously carried out in an autoclave under overpressure. When employing compounds of the formula VIII which contain a primary ester in the radical $R^2$, such as, for example, methyl or ethyl esters, the simultaneous conversion of the ester into the corresponding amide function can also be achieved using an appropriate excess of amine and, if desired, elevation of the reaction temperature.

Compounds of the formula Ia having a free carboxylic acid function in $R^2$ can be converted into the corresponding amides after activation of the carboxyl group using primary and secondary amines and also using carboxylprotected amino acids or lower peptides as reaction components. Methods known from peptide chemistry are advantageously used for the activation, such as, for example, the hydroxybenzotriazole/dicyclohexylcarbodiimide method (W. König, R. Geiger, Chem. Ber. 103 (1970), 788–798 and 2034–2040; Z. Naturforsch. 216 (1966) 426), activation by means of propanephosphonic anhydride (PPA) (Angew. Chem. Int. Ed. 19 (1980) 133) or by means of methylethylphosphonic anhydride (MEPA) (U.S. Pat. No. 4,426,325), it also being possible to use chlorinated hydrocarbons, and also formamide and dimethylformamide as solvents in addition to aliphatic and cyclic ethers, and preferably tertiary amines, such as, for example, triethylamine, N-ethylmorpholine or pyridine as auxiliary bases, while the reaction is carried out in the temperature range from about −10° C. to +50° C., preferably from about 0° C. to +20° C. Compounds of the formula Ia having free amino groups in the radical $R^1$ and a preferably protected carboxyl group in $R^2$ can be converted into the amides or peptides using amino acids protected on the nitrogen, lower peptides and other carboxylic acid derivatives capable of acylation in principally the same manner. It is obvious that when using an suitable selective protecting group technique known in principle from peptide chemistry any desired additional amino acids can be condensed into the $R^1$ and in the $R^2$ side chain of the compounds Ia.

If the peptide or other acyl derivatives are desired in the form of free amino or carboxylic acid functions, the corresponding protecting groups can be removed singly or, alternatively, together in the ways already described above. Thus, for example, by using strong acids, such as, for example, hydrochloric or hydrobromic acid in aliphatic primary alcohols, both the N-urethane protecting groups which may be present can be removed and also, at the same time, an ester group present in $R^2$, such as, for example, an alkyl, tert.-butyl or benzyl ester can be transesterified to the corresponding esters of the alcohol used.

For the synthesis of compounds of the formula Ib, the 1,3-dipolar cycloaddition described for Ia according to Mukaiyama can in principle be used starting from pentenoic or pentynoic acid derivatives and nitroethanol derivatives appropriately protected on the oxygen. After removal of the oxygen protecting group, as described above, the hydroxyl function is converted into an activated derivative, which is carried out, for example, by reaction with thionyl chloride or phosphorus oxychloride to give the 3-chloromethylisoxazole or -isoxazoline. The reagent used in this reaction is employed in equimolar amounts or preferably in an up to five-fold excess. Suitable solvents are halogenated hydrocarbons or preferably aliphatic ethers, such as, for example, diethyl ether or tetrahydrofuran, and the reaction temperature can be about 0° to +60° C., but preferably about 20° to 40° C. The activated derivative is then reacted with ammonia or an appropriately substituted amine to give the optionally substituted 3-aminomethyl derivative, which is preferably carried out by the use of a 2 to 100-fold excess of amine in a lower alcohol, for example, methanol or ethanol in a temperature range of 0° C. up to the boiling point of the solvent used. In order to avoid simultaneous amide formation when using alkyl ester-substituted heterocycles, temperatures of about 0° to +20° C. and the addition of catalytic amounts of tetrabutylammonium iodide have proved suitable. If a free carboxylic acid function is desired in the substituents in the 5-position, the ester group additionally present can be hydrolyzed by the methods described above or known from the literature. If it is then intended to carry out further reactions on the carboxyl substituent, the prior protection of a primary or secondary amino group with one of the N-protecting groups described above is recommended. By appropriate choice of the protecting groups, the variations of the radicals $R^1$ and $R^2$ described for Ia can thus collectively also be used for compounds of the formula Ib.

For conversion into quaternary ammonium derivatives, compounds of the formula Ia or Ib which carry a primary, secondary or tertiary amino group in $R^1$ are preferably reacted with an excess of an alkylating agent, for example an alkyl halide, a mesylate or a tosylate, in this case preferably an alkyl iodide, and a base, such as, for example, alkali metal carbonate or hydroxide, in dipolar aprotic solvents, such as, for example, methanol or ethanol with water, at temperatures of about 0° C. to +50° C. In the case of the preferred use of alkyl iodides, the resulting tetraalkylammonium iodide can be supplied directly for its pharmacological use.

If the compounds of the formulae Ia and Ib occur in diastereoisomeric or enantiomeric forms and are obtained in the chosen synthesis as their mixtures, resolution into the pure stereoisomers is carried out either by chromatography on an optionally chiral support material, or, if the racimic compounds of the formulae Ia and Ib are capable of salt formation, by fractional crystallization of the diastereomeric salts formed with an optically active base or acid as auxiliary. Also, in the case of peptides of esters of chiral alcohols of the formula Ia, the chirality of the amino acid or alcohol radical incorporated in the enantiomerically pure form can be utilized for the resolution of the diastereomers. Suitable chiral stationary phases for the thin-layer or column-chromatrographic resolution of enantiomers of the 2-isoxazolines having an asymmetric carbon atom in the 5-position and as a rule obtained as a racemate area, for example, modified silica gel supports (so-called Pirkle phases) and high-molecular-weight carbohydrates, such as, for example, triacetylcellulose. For analytical purposes, gas-chromatographic methods on chiral stationary phases can also be used after appropriate derivatization known to the person skilled int he art. For the enantiomeric resolution of the racemic carboxylic acids, phosphonic acids and phosphinic acids, the disastereomeric salts of different solubility are formed with an optically active base, as a rule a commercially available base, such as, for example, (−)-nicotine, (+)- and (−)-phenylethylamine, quinine bases, L-lysine or L- and D-arginine, the less soluble component is isolated as a solid, the more easily soluble diastereomer is precipitated from the mother liquor, and the pure the disasteromeric salts thus obtained. In principally the same manner, the racemic amino compounds of the formulae Ia and Ib can be converted into the pure enantiomers using optically active acids, such as, for example, (+)-camphor-10-sulfonic acid, optionally hydroxy-substituted D- and L-tartaric acids, D- and L-lactic acid and (+)- and (−)-mandelic acid. The use of chiral esters of the amino compounds employed for this purpose often favors the separation of the diastereomeric salts by fractional crystallization.

The pharmaceuticals according to the invention which, as active compounds, contain the compounds of the formulae Ia, Ib or Ic

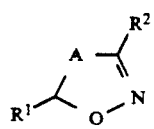
(Ia)

-continued

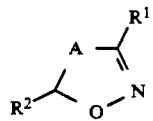
(Ib)

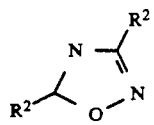
(Ic)

in which
$R^1$ is 2-, 3- or 4-pyridyl or a radical of the formula II

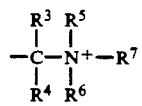
(II)

in which
$R^3$ and $R^4$ independently of one another are hydrogen or $C_1$-$C_4$-alkyl;
$R^5$ is a free electron pair or hydrogen;
$R^6$ and $R^7$ independently of one another are hydrogen; $C_1$-$C_6$-alkyl; $C_3$-$C_6$-cycloalkyl; $C_2$-$C_{12}$-aryl-$C_1$-$C_4$-alkyl; carbamimidoyl; $C_1$-$C_6$-alkylcarbonyl, $C_1$-$C_4$-alkenylcarbonyl, $C_1$-$C_6$-alkyloxycarbonyl, $C_6$-$C_{12}$-aryl-$C_1$-$C_4$--alkylcarbonyl, $C_6$-$C_{10}$-aryl-$C_1$-$C_4$-alkyloxycarbonyl, or the radical of a naturally occurring a-amino acid or c-aminobutyric acid (Gaba) which can be substituted by $C_1$-$C_6$-alkyl, hydroxyl, halogen, amino or nitro; or
$R^6$ and $R^7$, together with the nitrogen atom linking them, form a five- to seven-membered heterocycle, in which a carbon atom can be replaced by a sulfur, oxygen or nitrogen atom; or
$R^5$, $R^6$ and $R^7$ independently of one another are $C_1$-$C_4$-alkyl or $C_3$-$C_6$-cycloalkyl, or $R^6$ and $R^7$, together with the nitrogen atom linking them, for a six- to twelve-membered heterocycle;
$R^2$ is a radical of the formula III $$-(CH_2)_n-X$$  (III)

in which
n is 0 or an integer from 1 to 4;
X is hydroxyl; $C_1$-$C_4$-alkyloxy; carboxyl; haloformyl; formyl; oxyimino; $C_1$-$C_{12}$-alkoxycarbonyl; benzyloxycarbonyl or $C_3$-$C_6$-cycloalkyloxycarbonyl, which can be monosubstituted or polysubstituted by $C_1$-$C_6$-alkyl; or carbonyl which is linked by a peptide bond to a naturally occurring a-amino acid, c-aminobutyric acid or a dipeptide, or aminocarbonyl in which amino can be mono- or disubstituted by $C_1$-$C_6$-alkyl or monosubstituted by phenyl-$C_1$-$C_6$-alkyl, or both amino radicals, together with the nitrogen atom linking them, form a five- to seven-membered heterocycle in which a carbon atom can be replaced by an oxygen or nitrogen atom;
or X is a group of the formula IV

in which

Y and Z independently of one another are hydroxyl, $C_1$-$C_4$-alkyl or $C_1$-$C_4$-alkyloxy; and A is a C,C-single or a C,C-double bond;

if appropriate in stereoisomerically pure form and/or as physiologically tolerable salts, either by themselves, for example in microcapsules, in mixtures with one another or preferably in combination with suitable pharmaceutical excipients, diluents and/or other auxiliaries, can be administered parenterally, rectally or orally. Suitable solid or liquid pharmaceutical preparation forms are, for example, granules, powders, coated tablets, tablets, (micro)capsules, suppositories, syrups, elixirs, suspensions, emulsions, drops or injectable solutions and preparations having protracted release of active compound, in whose preparation auxiliaries, such as excipients, disintegrants, binders, coating agents, swelling agents, glidants or lubricants, flavorings, sweeteners or solubilizers are used. Commonly used auxiliaries which may be mentioned are, for example, magnesium carbonate, titanium dioxide, lactose, mannitol and other sugars, talc, lactoprotein, gelatin, starch, cellulose and its derivatives, animal and vegetable oils, such as cod liver oil, sunflower oil, groundnut oil or sesame oil, polyethylene glycols and solvents, such as, for example, sterile water, physiological saline solution and monohydric or polyhydric alcohols, for example glycerol. For the preparation of aqueous solutions of the strongly acid carboxylic, phosphonic and phosphinic acids according to formulae Ia and Ib, the active compound is expediently formulated such that it is present in salt form having a physiologically tolerable pH.

The pharmaceutical preparations are preferably produced and administered in dosage units, each unit containing a specific dose of at least one compound according to formulae Ia and Ib, if appropriate in stereoisomerically pure and/or salt form, as the active component. For solid dosage units, such as tablets, capsules, coated tablets or suppositories, this dose can be up to about 1,000 mg, but preferably about 50 to 300 mg, and for injection solutions in ampoule form up to about 300 mg, but preferably about 10 to 100 mg. For the treatment of an adult patient of about 70 kg weight—depending on the activity of the compounds according to formulae Ia and Ib, daily doses of about 50 to 3,000 mg of active compound, preferably about 150 to 1,000 mg, for oral administration and of about 50 to 1,000 mg, preferably about 100 to 300 mg, for intravenous administration are indicated for humans and animals. Under certain circumstances, however, higher or lower daily doses may also be appropriate. The administration of the daily dose can be carried out either by administration once in the form of a single dosage unit or else of several smaller dosage units and also by repeated administration of subdivided doses at specific intervals. Finally, the compounds of the formulae Ia and Ib, their optionally stereoisomeric forms and/or, if appropriate, their physiologically tolerable salts can also be combined together with other suitable active compounds, for example circulation-promoting substances, platelet aggregation inhibitors, thrombocyte aggregation inhibitors and calcium antagonists for the production of the abovementioned pharmaceutical preparation forms.

EXAMPLES

The following examples illustrate the invention without restricting it in its scope.

The structure of the compounds described below were confirmed by elemental analyses, IR, $^1$H-NMR and $^{13}$C-NMR spectra. The d values of the NMR spectra shown below are indicated in ppm and the coupling constants J in Hz. The structural formulae of the preparation examples described below are collated in Table 1.

TABLE 1

Structural formulae of the Examples

| Example. No. | Formula |
|---|---|
| 1 | 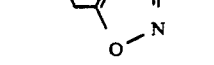 |
| 2 | 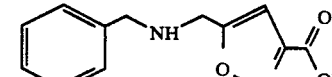 |
| 3 | 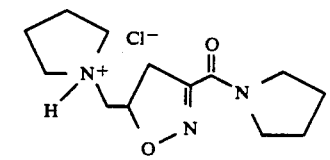 |
| 4 | 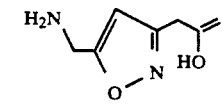 |
| 5 | 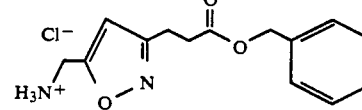 |
| 6 | 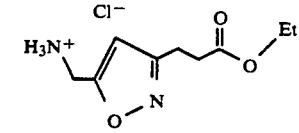 |
| 7 | 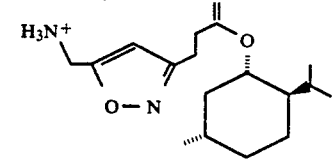 |
| 8 | 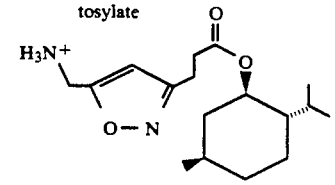 |

TABLE 1-continued

Structural formulae of the Examples

| Example. No. | Formula |
|---|---|
| 9 | (tosylate salt) structure with H₃N⁺–CH₂–C(=N–O)–CH=C–CH₂–C(=O)–O–(trimethylcyclohexyl) |
| 10 | Cl⁻ salt; H₃N⁺–CH₂–C(=N–O)–CH=C–CH₂–CH₂–P(=O)(OEt)(Me) |
| 11 | H₃N⁺–CH₂–C(=N–O)–CH=C–CH₂–C(=O)–OMe, Cl⁻ |
| 12 | H₂N–CH₂–C(=N–O)–CH=C–CH₂–C(=O)OH |
| 13 | Me₂C(NH₂)–C(=N–O)–CH=C–CH₂–C(=O)OH |
| 14 | PhCH₂–NH–CH₂–C(=N–O)–CH=C–CH₂–C(=O)OH |
| 15 | Me₂N–CH₂–C(=N–O)–CH=C–CH₂–C(=O)OH |
| 16 | Br⁻ salt; H₃N⁺–CH₂–C(=N–O)–CH=C–CH₂–CH₂–P(=O)(OH)(Me) |
| 17 | AcNH–CH₂–C(=N–O)–CH=C–CH₂–C(=O)OH |
| 18 | Me₃N⁺–CH₂–C(=N–O)–CH=C–CH₂–C(=O)–O–(menthyl), I⁻ |
| 19 | Me₃N⁺–CH₂–C(=N–O)–CH=C–CH₂–C(=O)–O–(menthyl), I⁻ |
| 20 | PhCH₂–CH(NH₃⁺)–C(=O)NH–CH₂–C(=N–O)–CH=C–CH₂–C(=O)–O–(menthyl), Cl⁻ |
| 21 | PhCH₂–CH(NH₃⁺)–C(=O)NH–CH₂–C(=N–O)–CH=C–CH₂–C(=O)–O–(menthyl), Cl⁻ |
| 22 | PhCH₂–CH(NH₃⁺)–C(=O)NH–CH₂–C(=N–O)–CH=C–CH₂–C(=O)–OMe, Cl⁻ |
| 23 | H₂N–C(=NH)–NH–CH₂–C(=N–O)–CH=C–CH₂–C(=O)OH |
| 24 | H₂N–CH₂–C(=N–O)–CH=C–CH₂–C(=O)–NH–CH₂–C(=O)OH |
| 25 | H₃N⁺–CH₂–C(=N–O)–CH=C–CH₂–CH₂–OH, Cl⁻ |

TABLE 1-continued

Structural formulae of the Examples

| Example No. | Formula |
|---|---|
| 26 | ammonium salt, bis-isoxazole structure with two carboxylates and NH bridge |
| 27 | tosylate, menthyl ester of aminomethyl-oxazine carboxylate |
| 28 | tosylate, menthyl ester (diastereomer) |
| 29 | H$_2$N-CH$_2$-[isoxazoline]-CH$_2$-COOH, racemate |
| 30 | (−)-enantiomer |
| 31 | (+)-enantiomer |
| 32 | AcNH-CH$_2$-[isoxazoline]-CH$_2$-COO$^-$ Na$^+$ |
| 33 | 2-pyridyl-[isoxazoline]-CH$_2$-COOH |
| 34 | tosylate, methyl ester H$_3$N$^+$-CH$_2$-[isoxazoline]-CH$_2$-CO$_2$Me |
| 35 | H$_2$N-CH$_2$-[isoxazoline]-COOH |
| 36 | H$_2$N-CH$_2$-CH(O-N)-CH$_2$-C(=O)NH$_2$, trifluoroacetate |
| 37 | Cl$^-$, H$_3$N$^+$-CH$_2$-[isoxazoline]-C(=O)-N(pyrrolidine) |
| 38 | Cl$^-$, H$_3$N$^+$-CH$_2$-[isoxazoline]-C(=O)-N(morpholine) |
| 39 | Cl$^-$, H$_3$N$^+$-CH$_2$-[isoxazoline]-C(=O)-NMe$_2$ |
| 40 | Cl$^-$, 2-pyridinium-CH(-)-CH$_2$-[isoxazoline]-CH$_2$OH |
| 41a / 41b | H$_3$N$^+$-CH$_2$-[isoxazoline]-C(=O)-NH-CH(Me)Ph, trifluoroacetate |
| 42 | H$_2$N-CH$_2$-C(=CH-)-[oxime]-CH$_2$OH |
| 43 | Me-NH$_2^+$-Me Cl$^-$, -CH$_2$-[oxime]-CH$_2$OH |
| 44 | Me$_2$C(NH$_2$)-C(=CH-)-[oxime]-COOH |
| 45 | Me$_3$N$^+$ I$^-$, -CH$_2$-[oxime]-CH$_2$OH |

TABLE 1-continued

Structural formulae of the Examples

| Example. No. | Formula |
|---|---|
| 46 | 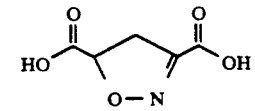 |
| 47 | |
| 48 | |
| 49 | |
| 50 | |
| 51 | |
| 52 | |
| 53 | |
| 54 | |
| 55 | |
| 56 | 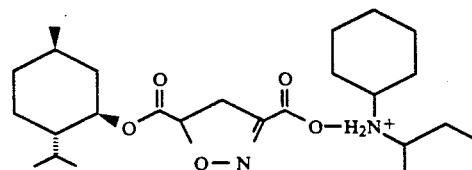 |
| 57 | |
| 58 | |
| 59 | |

Example 1: 3-Carboxy-5-aminomethylisoxazole a) N-tert.-Butoxycarbonylproparglyamine 24 g (0.44 mol) of propargylamine and 44.5 g (0.44 mol) or triethylamine are initially introduced into 350 ml of diethyl ether, a solution of 96 g (0.44 mol) of di-tert.-butyl dicarbonate in 150 ml of diethyl ether is added dropwise with ice-cooling and the mixture is then stirred at room temperature for about 2 hours. It is washed with saturated ammonium chloride solution until the pH is 6 and then with water. After drying and concentrating, the product can be crystallized from petroleum ether in a freezer compartment.

Yield: 62 g, melting point: 41° C.

b) Cycloaddition with ethoxycarbonylnitrile oxide

Ethyl chloroximidoacetate is prepared starting from glycine ethyl ester hydrochloride according to a literature procedure (G. S. Skinner, J. Am. Chem. Soc. 46 (1924), 731). 14.55 g (0.096 mol) of this product are added dropwise, dissolved in 100 ml of tetrahydrofuran, at room temperature to a solution of 17.07 g (0.11 mol) of the protected propargylamine from a) and 11.14 g (0.11 mol) of triethylamine in 400 ml of diethyl ether during the course of 5 hours. The mixture is stirred overnight, washed with dil. ammonium chloride solution and water, dried and concentrated in vacuo. Yield: 25 g. The product ethyl 5-tert.-butoxycarbonyaminomethylisoxazole-3-carboxylate can be further purified by crystallization from ethyl acetate/petroleum ether, resulting in a melting point of 72° C.

c) Hydrolysis of carboxylic acid ester 9.75 g (0.036 mol) of the products from b) are dissolved in 80 ml of ethanol, 75 ml of 1 N NaOH are added and the mixture is stirred at room temperature with TLC checking until hydrolysis is complete. After removing the ethanol in vacuo, the mixture is acidified to pH 2-3 using dil. hydrochloric acid, extracted several times with dichloromethane or ethyl acetate, washed with a little water, dried and concentrated. Crystallization form diethyl ether/petroleum ether yields 7.18 g of analytically pure product of melting point 120°-121° C.

d) Cleavage of the tert.-butoxycarbonyl protecting group 6.9 g of the product from c) are dissolved in 125 ml of dichloromethane, about 25 ml of trifluoroacetic acid are added with ice-cooling and the mixture is then stirred at room temperature with TLC checking until the reaction is complete. After concentrating in vacuo, the excess of trifluoroacetic acid is removed several times using dichloromethane as entrainer and the remaining solid residue is thoroughly stirred with diethyl ether. 7.16 g of the analytically pure trifluoroacetate of 5-aminomethyl-3-carboxyisoxazole are obtained. For conversion into the betaine, the salt is dissolved in water, the solution is adjusted to pH 7 using dil. ammonia solution and the betaine is precipitated by slow addition of acetone. Melting point: 153° C.

$^1$H-NMR (trifluoroacetate in DMSO-d$_6$): $\delta$=4.5 (s, 2H, CH$_2$-N), 7.1 (s, 1H, 4-H), 9.4 (vb, 5 acidic H).

Example 2: 5-Benzylaminomethyl-3-carboxyisoxazole

N-Benzylproparglyamine is protected by means of di-tert.-butyl dicarbonate as described in Example 1a). Cycloaddition with ethoxycarbonylnitrile oxide, hydrolysis of the ester group, removal of the N-protecting group and precipitation of the betaine from the trifluoroacetate initially obtained are carried out as described in Examples 1)-1d). The analytically pure product obtained has a melting point of 128° C.

$^1$H-NMR (betaine in D$_2$O/NaOD): $\delta$=3.6 and 3.7 (2s, 2H each, 2 CH$_2$), 6.3 (s, 1H, 4-H), 7.0-7.3 (m, 5 aryl-H).

Example 3:
5-Pyrrolidinomethyl-3-pyrrolidinocarbonyl-2-isoxazoline hydrochloride a) Cycloaddition with allyl bromide 48.39 g (0.4 mol) of allyl bromide and 45.47 g (0.3 mol) of ethyl chlorooximidoacetate are initially introduced into 700 ml of diethyl ether and a solution of 35.44 g (0.35 mol) of triethylamine in 200 ml of ether is added dropwise during the course of 6 hours. The mixture is stirred overnight, the precipitate salt is filtered off, and the filtrate is washed with dil. ammonium chloride solution and with water to the point of neutrality. After drying and concentrating, 65 g of 5-bromomethyl-3-ethoxycarbonyl-2-isoxazoline remain, which can be recrystallized from diethyl ether/petroleum ether. Melting point: 54° C.

b) Substitution reaction with pyrrolidine 11.8 g (0.05 mol) of the product from a) are dissolve in 200 ml of ethanol and 82 ml of pyrrolidine and the mixture is heated to reflux for 2.5 hours. After concentrating in vacuo, the residue is taken p in 2 N hydrochloric acid, the solution is washed with diethyl ether, the aqueous phase is rendered neutral and extracted several times with dichloromethane, the organic phase is dried and concentrated, and finally the desired product is precipitated from diethyl ether by the addition of ethanolic hydrochloric acid. 10.7 g of analytically pure hydrochloride of melting point 207° C. remain.

$^1$H-NMR (hydrochloride in CDCl$_3$): $\delta$=1.8-2.4 (m, 8H, 4 CH$_2$), 2.8-4.0 (m, 12H, 4-H and 4 CH$_2$-N), 5.3-5.9 (mc, 1H, 5-H).

Example 4: 5-Aminomethylisoxazole-3-acetic acid a) ethyl 3-hydroxyimidopropionate The synthesis is carried out in analogy to a literature procedure (U.S. Pat. No. 3,499,278), starting from ethyl formate and ethyl acetate.

b) Cycloaddition with N-tert-butoxycarbonylpropargylamine 6.6 g (0.05 mol) of the product form a), dissolved in 100 ml of dichloromethane, are initially introduced at 0° C. and a solution of 6 g (0.055 mol) of tert.-butyl hypochlorite in 20 ml of dichloromethane is added dropwise during the course of 30 min. The mixture is stirred for 1 hour after removing the cooling bath, a solution of 7.8 g (0.05 mol) of N-tert.-butoxycarbonylpropargylamine in 50 ml of dichloromethane is added, a solution of 8.3 ml (0.05 mol) of triethylamine in 100 ml of dichloromethane is then added dropwise during the course of 6 hours and the mixture is stirred overnight. The reaction solution is washed with water, dil. citric acid and water again, dried and concentrated. 14.2 g of an oil which can be further purified by chromatography on silica gel using tert.-butyl methyl ether and petroleum ether (1:1) as the eluent are obtained.

c) Hydrolysis of the ethyl ester and cleavage of the N-protecting group

These two steps are carried out analogously to Examples 1c) and 1d). The trifluoroacetate of the product which remains as an oil is dissolved in acetone, adjusted to a pH of 5 to 6 using alcoholic ammonia solution, and the precipitated betaine is filtered off with suction and dried in vacuo. Starting form 8 g of step b), 3.5 g of analytically pure betaine of melting point 216° C. are obtained.

$^1$H-NMR (betaine in D$_2$O): $\delta$=3.8 (s, 2H, CH$_2$), 4.3 (s, 2H, CH$_2$-N), 6.5 (s, 1H, 4-H).

For the cycloaddition step of Examples 5 to 11 below, nitrobutyric acid building blocks are dehydrated in a variant of the method of Mukaiyama (J. Am. Chem. Soc. 82 (1960), 5339-5342) by means of isocyanates. The synthetic route, starting from acrylic acid derivatives and nitromethane, is described below by way of example for benzyl nitrobutyrate as representative of the non-commercially available derivatives. By using appropriately substituted vinylphosphinic acid and vinyl phosphinic acid esters, this method can also be applied to 4-nitropropylphosphinic and -phosphonic acid derivatives.

286 g (2.65 mol) of benzyl alcohol and 366 ml (2.65 mol) of triethylamine are initially introduced into 3 l of tert.-butyl methyl ether with ice-cooling. 240 g (2.65 mol) of acryloyl chloride are added dropwise, the mixture is stirred at room temperature for 2 hours, and the organic phase is washed several times with water, dried and concentrated in vacuo. The benzyl acrylate which is obtained in quantitative yield is added dropwise at a bath temperature of 70° C. to an initially introduced solution of 2.5 l of nitromethane and 10 ml of 1,8-diazabicyclo-[5.4.0]undec-7-ene (DBU), the pH which may drop owing to traces of acrylic acid being kept constant by addition of appropriate amounts of DBU. After the exothermic reaction has subsided (temperature increase to 90° C.), the mixture is allowed to cool for 60 min, washed several times with dil. aq. hydrochloric acid and water, dried, and concentrated in vacuo, 464 g of a reddish-brown oil remaining, which can be employed for the cycloaddition without further purification.

The nitro compounds used below, for example, can be prepared in the same way: methyl and ethyl 4-nitrobutyrate tert.butyl 4-nitrobutyrate (+)- and (−)-methyl 4-nitrobutyrate cis-(3,3,5)-trimethylcyclohexyl 4-nitrobutyrate dimethyl and diethyl 3-nitropropylphosphonate (starting from vinylphosphonic acid esters) ethyl 3-nitropropyl-P-methylphosphinate (starting from ethyl vinyl-P-methylphosphinate).

Example 5: Benzyl 5-aminomethylisoxazole-3-propionate hydrochloride a) Cycloaddition 78 g (0.5 mol) of N-tert.-butoxycarbonylproparglyamine are initially introduced into 2 l of toluene at 70° C. together with 2.5 ml of triethylamine and 96 g (0.6 mol) of phenylene diisocyanate. 112 g (0.5 mol) of the benzyl 4-nitrobutyrate described above, to which 2.5 ml of triethylamine are added, are added dropwise in the course of 5 hours. The mixture is stirred at room temperature overnight, and precipitated urea is filtered off with suction and washed with dichloromethane. After concentrating, 200 g of an oily crude product remain, which can be further purified by chromatography on silica gel (eluent: petroleum ether/tert.-butyl methyl ether mixtures).

b) Removal of the N-protecting group 25 g (0.064 mol) of the product obtained under a) are treated at room temperature with a solution of 75 ml of trifluoroacetic acid in 375 ml of dichloromethane until the formation of gas has ceased (about 1 hour). The trifluoroacetate which remains after concentrating is taken up in methanol and the hydrochloride is precipitated by addition of ethereal hydrochloric acid and can be converted into an analytically pure form by recrystallization from methanol/tert.-butyl methyl ether. Yield: 15 g; melting point: 172° C.

$^1$H-NMR (hydrochloride in DMSO-d$_6$): $\delta = 2.8$–3.0 (m, 4H, 2 CH$_2$), 4.2 (s, 2H, CH$_2$-N), 5.1 (s, 2H, CH$_2$-O), 6.6 (s, 1H, 4-H), 7.25–7.45 (m, 5 aryl-H).

Examples 6 to 11 of the formula Ia shown below in Table 2a, in which A is a C,C-double bond, are synthesized analogously to Example 5 by cycloaddition of appropriately substituted nitro compounds with N-tert.-butoxycarbonylproparglyamine and removal of the N-protecting group.

TABLE 2a

| Example | R$^1$ | R$^2$ | M.p. [°C.] | $^1$H-NMR, δ (ppm) | Notes |
|---------|-------|-------|------------|---------------------|-------|
| 6 | —CH$_2$—NH$_2$ × HCl | —(CH$_2$)$_2$—CO$_2$Et | 165 | (in MeOH-d$_4$): 1.27(t, J=6.5, 3H, OEt), 2.73 and 3.0(each mc, 2H, —CH$_2$—CH$_2$—) 4.13(q, J=6.5, 2H, OEt), 4.35(s, 2H, CH$_2$—N), 4.9(sb, 4H, NH$_3$$^+$), 6.6(s, 1H, 4-H) | |
| 7 | —CH$_2$—NH$_2$ × Tos-OH | —(CH$_2$)$_2$—COO-(3,3,5-trimethylcyclohexyl) | 157 | (in DMSO-d$_6$): 0.7(d, 3H, J=6.8, CH$_3$), 0.8-2.0(m, 15H, 2CH$_3$, 3CH$_2$—, 3CH), 2.3(s, 3H, Tos-OH), 2.7 and 2.9(each mc, 2H, —CH—CH—) 4.3(s, 2H, —CH$_2$—N), 4.5-4.7(dt, 1H, CHO), 6.5(s, 1H, 4-H), 7.1 u. 7.5(AA'BB', Tos-OH), 8.4 (acidi c H) | $a_D^{20} = +29.5°$ (c = 1, Et-OH) |
| 8 | —CH$_2$—NH$_2$ × Tos-OH | —(CH$_2$)$_2$—COO-(3,3,5-trimethylcyclohexyl) | 157–158 | NMR as Example 7 | $a_D^{20} = -28.9°$ (c = 1, Et-OH) |
| 9 | —CH$_2$—NH$_2$ × Tos-OH | —(CH$_2$)$_2$—COO-(3,3,5,5-tetramethylcyclohexyl) | 175 | (in DMSO-d$_6$): 0.7-2.0(m, 16H, 3CH$_3$, 3CH$_2$, 1CH), 2.3(s, Tos-OH), 2.65 u. 2.9(each mc, 2H, —CH$_2$—CH$_2$—) 4.3(s, 2H, CH$_2$—N), 4.7-4.9(mc, 1H, CHO), 6.5(s, 1H, 4-H), 4.1 u. 7.5(AA'BB', Tos-OH), 8.5(3 acide H) | racemate |

TABLE 2a-continued

| Example | R$^1$ | R$^2$ | M.p. [°C.] | $^1$H-NMR, δ (ppm) | Notes |
|---|---|---|---|---|---|
| 10 | —CH$_2$—NH$_2$ × HCl | —(CH$_2$)$_2$—P(=O)(Me)(OEt) | 134 | (in MeOH-d$_4$): 1.3(t, 3H, J=7, OEt), 1.5(d, 3H, J=13.8, P—Me), 2.7 and 3.0(jew, each mc, 2H, —CH$_2$—CH$_2$—), 4.1(mc, 2H, OEt), 4.35(s, 2H, CH$_2$—N), 6.6(s, 1H, 4-H) | |
| 11 | —CH$_2$—NH$_2$ × HCl | —(CH$_2$)$_2$—CO$_2$Me | 183 | (in DMSO-d$_6$): 2.7 and 2.9(each mc, 2H, —CH$_2$—CH$_2$—) 3.6(s, 3H, OCH$_3$), 4.2(s, 2H, CH$_2$—N), 6.6(s, 1H, 4-H), 8.9(3 acidic H) | |

Example 12: 5-Aminomethylisoxazole-3-propionic acid

The cycloaddition is carried out starting from tert.-butyl 4-nitrobutyrate and N-tert.-butoxycarbonyl-proparglyamine as described in Example 5. The crude product obtained is treated with an excess of trifluoroacetic acid in dichloromethane analogously to Example 5b), cleavage of both the ester and the urethane protecting group taking place at the same time. The residue which remains after concentrating is taken up in acetone, the solution is treated with activated carbon and filtered, and the pH is adjusted to 6 using conc. ammonia solution. The product which crystallizes out as the betaine is filtered off with suction after about 24 hours, washed with acetone and dried. It can be recrystallized from water/acetone if desired.

Melting point: 218° C. (with decomposition)
$^1$H-NMR (betaine in 1N NaOD): δ=2.5 and 2.9 (each t, 2H, J=7.5, —CH$_2$—CH$_2$—), 3.9 (s, 2H, CH$_2$-N), 6.3 (s, 1H, 4-H).

Example 13:
5-(1-Amino-1-methylethyl)isoxazole-3-propionic acid 3,3-Dimethylproparglyamine is provided with the tert.-butoxycarbonyl protecting group as described in Example 1a). Cycloaddition using tert.-butyl 4-nitrobutyrate is carried out as described in Example 5a). Removal of the protecting groups and conversion of the trifluoroacetate into the betaine analogously to Example 13 yields an analytically pure product of melting point 219° C.

$^1$H-NMR (betaine in D$_2$O): δ=1.7 (s, 6H, 2CH$_3$), 2.5 and 2.9 (each t, 2H, J=7.5, —CH$_2$—CH$_2$—), 6.4 (s, 1H, 4-H).

Example 14:
5-Benzylaminomethylisoxazole-3-propionic acid

N-Benzyl-N-tert.-butoxycarbonylproparglyamine provided with the BOC protective group analogously to Example 2 is reacted with tert.-butyl 4-nitrobutyrate as described in Example 5a), then the protecting groups are removed analogously to Example 12 and the product is precipitated as the betaine. Melting point: 153° C.

$^1$H-NMR (betaine in MeOH-d$_4$): δ=2.7 and 3.0 (each t, 2H, J=7.5, —CH$_2$—CH$_2$—), 3.85 and 3.93 (each s, 2H, 2CH$_2$-N), 6.2 (s, 1H, 4-H), 7.2-7.4 (m, 5 aryl-H).

Example 15:
5-Dimethylaminomethylizoxazole-3-propionic acid

Cycloaddition is carried out starting from N,N-dimethylproparglyamine and tert.-butyl 4-nitrobutyrate as described in Example 5a). The removal of the tert.-butyl ester group is carried out analogously to Example 12. The crude product obtained is purified by chromatography on silica gel (eluent: tert.-butyl methyl ether/methanol mixture with the addition of 1% aq. ammonia), and the betaine is then precipitated from acetone by adjusting the pH to 6.5 by means of trifluoroacetic acid. Melting point: 85° C.

$^1$H-NMR (betaine in DMSO-d$_6$): δ=2.2 (s, 6H, 2 N-Me), 2.6 and 2.76 (each mc, 2H, —CH$_2$—CH$_2$—), 3.6 (s, 2H, CH$_2$—N), 6.3 (s, 1H, 4-H).

Example 16:
2-(5-Aminomethylisoxazol-3-yl)ethyl-2-(-methyl)phosphinic acid hydrochloride 5 g (0.019 mol) of the product from Example 10 are treated at room temperature with a 33% strength solution of HBr in glacial acetic acid for about 70 hours. After concentrating in vacuo, the residue is thoroughly stirred with acetone and then recrystallized from acetone/water. Yield: 3 g of hydrobromide; melting point: 198° C.

$^1$H-NMR (hydrobromide in DMSO-d$_6$): δ=1.3 (d, J=14, 3H, P-Me), 1.95 and 2.85 (each mc, 2H, —CH$_2$—CH$_2$—), 4.3 (s, 2H, CH$_2$-N), 6.6 (s, 1H, 4-H), 8.55 (4 acidic H).

Example 17: 5-Acetamidomethylisoxazole-3-propionic acid 7 g (0.04313 mol) of the product from Example 12 are suspended in a solution of 70 ml of acetic anhydride in 140 ml of pyridine with intensive stirring, the starting material slowly going into solution. After completion of the reaction (TLC checking), the mixture is concentrated in vacuo and the product is crystallized from acetone. Yield: 5.5 g; melting point: 134° C.

$^1$H-NMR (in DMSO-d$_6$): δ=1.9 (s, 3H, Ac), 2.8-3.05 (m, 4H, —CH$_2$—CH$_2$—), 4.3 (d, J=6, 2H, CH$_2$-N), 6.3 (s, 1H, 4-H), 8.5 (t, J=6, 1H, NH).

Example 18: (—)-Menthyl 5-trimethylammoniomethylisoxazole-3-propionate iodide 9.6 g (0.02 mol) of the product from Example 8 are initially introduced into 250 ml of acetone together with 16.6 g (0.12 mol) of potassium carbonate. After dropwise addition of 6.25 ml (0.1 mol) of methyl iodide, the mixture is stirred at room temperature for 3 days. Precipitate salt is filtered off, the filtrate is concentrated and the residue is crystallized from water. Yield: 6.5 g; melting point: 131° C. (dec.).

$[\alpha]_D^{20} = -40.0°$ (c=1 in ethanol)

$^1$H-NMR (iodide in MeOH-d$_4$): δ=0.7 (d, J=7, 3H, Me), 0.85-2.05 (m, 15H, 2Me, 3CH$_2$, 3CH), 2.77 and 3.05 (each mc, 2H, —CH$_2$—Ch$_2$—), 3.2 (s, 9H NMe$^{3+}$), 4.7 (mc, 1H, CHO), 4.9 (s, 2H, CH$_2$-N), 6.85 (s, 1H, 4-H).

Example 19: (+)-Menthyl 5-trimethylammoniomethylisoxazole-3-propionate iodide The product from Example 7 is reacted with methyl iodide as described in Example 18 and the product is crystallized from water. Melting point: 130° C.
$[\alpha]_D^{20} = +39.3°$ (c=1 in ethanol)
$^1$H-NMR: as Example 18

Example 20: (+)-Menthyl 5-(L-phenylalanylamino)methylisoxazole-3propionate hydrochloride a) Peptide coupling

12.8 g (0.042 mol) of the base form from Example 7 are initially introduced into 200 ml of tetrahydrofuran. After adding 11.05 g (0.042 mol) of N-tert.-butoxycarbonyl-L-phenylalanine and 26.7 ml (0.21 mol) of N-ethylmorpholine, 26.9 ml (=0.042 mol) of a 50% strength solution of propanephosphonic anhydride in dichloromethane are added dropwise at 0° C. and the mixture is then stirred for 4 hours while warming to room temperature. It is diluted with ethyl acetate and the organic phase is washed with citric acid and water, dried and concentrated. The product can be crystallized from tert.-butyl methyl ether/petroleum ether.

Yield: 17.5 g; melting point 122° C.

b) Cleavage of the protecting group

Removal of the N-protecting group is carried out as described in Example 5b). The residue which remains is taken up in ethyl acetate and, by shaking with 1 N sodium hydroxide solution, converted into the base, which can be crystallized from petroleum ether.

Analytically pure hydrochloride can be precipitated from methanol by means of ethereal hydrochloric acid. The melting point is 148° C.

$[\alpha]_D^{20} = +15.9°$ (c=1 in water)

$^1$H-NMR (hydrochloride in MeOH-d$_4$): δ=0.7 (d, 3H, J=7, Me), 0.75-2.0 (m, 15H, 2Me, 3CH$_2$, 3CH), 2.7 and 2.95 (each mc, 2H, —CH$_2$—CH$_2$—), 3.0-3.3 (mc, 2H, Ph-CH$_2$), 4.1 (mc, 1H, CHN), 4.35-4.8 (mc, 3H, CHO and CH$_2$-N), 6.1 (s, 1H, 4-H), 7.2-7.45 (m, 5 aryl-H).

Example 21: (−)-Menthyl 5-(L-phenylalanylamino)methylisoxazole-3-propionate hydrochloride Starting from the product from Example 8, the peptide coupling and the protecting group cleavage are carried out analogously to Example 20. The product precipitated as the hydrochloride has a melting point of 135° C.

$[\alpha]_D^{20} = -43.5°$ (c=1 in water).

$^1$H-NMR: as Example 20

Example 22: Methyl 5-(L-phenylalanylamino)methylisoxazole-3-propionate hydrochloride Starting from the product from Example 11, the peptide coupling and the protecting group cleavage are carried out analogous to Example 20. The product precipitated as the hydrochloride has a melting point of 133° C.

$[\alpha]_D^{20} = +3.6°$ (c=1 in water).

$^1$H-NMR (hydrochloride in MeOH-d$_4$): δ=2.65 and 2.9 (each mg, 2H, —CH$_2$—CH$_2$—), 3.1 (mc, 2H, Ph-CH$_2$), 3.63 (s, 3H, Ome), 4.03 (t, J=7.5, 1H, CHN), 4.3-4.55 (AB, J=16, 2H, CH$_2$-N), 6.0 (s, 1H, 4-H), 7.1-7.4 (m, 5 aryl-H).

Example 23: 5-Guanidinomethylisoxazole-3-propionic acid 6.8 g (0.04 mol) of the product from Example 12 are dissolved in 40 ml of 1 N sodium hydroxide solution and 5.56 g of S-methylisothiourea hydrogen sulfate (=0.04 mol of urea) in solid form are added. The mixture is stirred at room temperature for 24 hours, during which the product slowly crystallizes out, and is filtered off with suction and washed thoroughly with water. Yield: 2.8 g; melting point >297° C.

$^1$H-NMR (betaine in TFA-d$_1$): δ=2.95 and 3.22 (each mc, 2H, —CH$_2$—CH$_2$—), 4.7 (s, 2H, CH$_2$-N), 6.5 (s, 1H, 4-H).

Example 24: N-(5-Aminomethylisoxazol-3-yl)propionylglycine a) Selective ester cleavage

100 g of the cycloadduct from Example 5a) (crude product) are dissolved in 500 ml of isopropanol and 500 ml of 1 N sodium hydroxide solution for the hydrolysis of the benzyl ester, and after completion of the reaction (TLC checking), the aqueous solution is extracted twice with tert.-butyl methyl ether and acidified using aq. hydrochloric acid with ice-cooling and the product is extracted from the water phase several times using ethyl acetate. After drying and concentrating, it is crystallized from tert.-butyl methyl ether. Yield: 32 g; melting point: 80° C.

b) Peptide coupling

11.6 g (0.043 mol) of the product from a) are dissolved in 210 ml of tetrahydrofuran and 210 ml of N,N-dimethylformamide together with 7.1 g (0.043 mol) of glycine benzyl ester and 27.23 ml (0.215 mol) of a 50% strength solution of propanephosphonic anhydride in dichloromethane are added dropwise with ice-cooling. The mixture is stirred at room temperature with TLC checking for about 5 hours, diluted with ethyl acetate and washed with citric acid and water. After drying and concentrating, 17 g of an oily product remain.

c) Hydrolysis of the ester group

12 g of the product from b) are dissolved in 390 ml of isopropaneol, and 150 ml of 1 N sodium hydroxide solution are added. After completion of the reaction, the mixture is acidified using hydrochloric acid with ice-cooling, the product is extracted several times with ethyl acetate and the organic phase is dried and concentrated, 5.9 g of an oil remaining.

d) Cleavage of the N-tert.-butoxycarbonyl protecting group

5 g of the product from c) are taken up in a mixture of 15 ml of trifluoroacetic acid and 75 ml of dichloromethane, the solution is concentrated in vacuo after about 1 hour, the residue is taken up using acetone and the solution is adjusted to a pH of 6.5 by means of conc. aq.

ammonia. The betaine is filtered off with suction and dried.

Yield: 2.5 g; melting point 204° C.

¹H-NMR (in D₂O): δ=2.65 and 3.0 (each t, 2H, J=7.6, —CH₂—CH₂—), 3.6 (s, 2H, Gly-CH₂), 4.3 (s, 2H, CH₂-N), 6.5 (s, 1H, 4-H).

Example 25: 5-Aminomethyl-3-(2-hydroxyethyl)isoxazole hydrochloride a) Cycloaddition

Cycloaddition is carried out starting from 38.8 g (0.25 mol) of N-tert.-butoxycarbonylpropargylamine and 39.56 (0.25 mol) of 3-nitropropyl tert.-butyl ether (compare R Öhrlein et al., Synthesis 1986, 535-538) analogously to Example 5a). The product 5-tert.-butoxycarbonylaminomethyl-3-(2-hydroxy)ethyl a yield of isoxazole is isolated in oily form in a yield of 61.6 g.

b) Cleavage of the protecting groups

The N- and O-protecting groups are cleaved by means of trifluoroacetic acid as described in Example 5b) and the solution is concentrated. For purification, the crude product in methanol is added to a column containing strongly acidic cation exchanger (H+ form), the column is washed with methanol, then the product is eluted with 4 N methanolic ammonia solution and the product fractions are concentrated. Analytically pure hydrochloride having a melting point of 163° C. can then be precipitated from methanol using ethereal hydrochloric acid.

¹H-NMR (hydrochloride in D₂O): δ=2.85 and 3.8 (each t, 2H, J=6, —CH₂—CH₂—), 4.3 (s, 2H, CH₂—N), 6.5 (s, 1H, 4-H).

Example 26: Bis(3-[2-carboxyethyl]isoxazol-5-ylmethyl)amine diammonium salt a) Cycloaddition

Diproparglyamine is provided with the N-tert.butoxycarbonyl protecting group as described in Example 1a). 30 g (0.16 mol) of this compound are subjected to 1,3-dipolar cycloaddition with 60 g (0.32 mol) of tert.-butyl 4-nitrobutyrate using 60 g (0.36 mol) of phenylene diisocyanate analogously to Example 5a). The 100 g of crude product obtained can be purified by chromatography on silica gel using tert.-butyl methyl ether/petroleum ether mixtures.

b) Cleavage of the protecting group

The cleavage of the BOC protecting group and of the tert.-butyl ether is carried out analogously to Example 5b) using trifluoroacetic acid. The residue which remains after concentrating is taken up in acetone and the ammonium salt is precipitated by addition of con. aq. ammonia. Yield: 15 g; melting point: 146° C. from 30 g of precursor.

¹H-NMR (ammonium slat in DMSO-d₆): δ=2.36 and 2.74 (each t, 2H, J=6.5, —CH₂—CH₂—), 3.8 (s, 2H, CH₂—N), 5.4 (b, NH⁴ +), 6.2 (s, 1H, 4-H).

Example 27: (+)-Menthyl 5-aminomethyl-2-isoxazoline-3-propionate toluene-4-sulfonate c) Cycloaddition

Allylamine is provided with the N-tert.-butoxycarbonyl protecting group as described in Example 1a). The product is isolated in solid form and has a melting point of 38° C. after concentrating. 41.1 g (0.26 mol) thereof are subjected to the cycloaddition with 72 g (0.26 mol) of (+)-menthyl 4-nitrobutyrate and 50.1 g (0.3 mol) of phenylene diisocyanate in analogy to Example 5a). 95 g of an oily crude product are obtained, which can be further purified analogously to Example 26a).

b) Cleavage of the BOC protecting group

The cleavage of the protecting group is carried out in analogy to Example 5b). The product is isolated from dil. sodium hydroxide solution as the base by extraction with tert.-butyl methyl ether and precipitated from tert.-butyl methyl ether as the tosylate by addition of one equivalent of toluene-4-sulfonic acid. According to GC analysis, a mixture of the two C-5 epimers is present in a ratio of about 1:1. Melting point: 144°-145° C.

¹H-NMR (tosylate in DMSO-d₆): δ=0.7 (d, J=6.8, 3H, Me), 0.18-1.95 (m, 15H, 2Me, 3CH₂, 3CH), 2.3 (s, Tos-OH), 2.55-3.3 (m, 8H, —CH₂—Ch₂—, CH₂-N, 4-H), 4.5-4.8 (m, 2H, 5-H and CHO), 7.1 and 7.66 (AA'BB', Tos-OH), 8.0 (acidic H).

Example 28: (−)-Menthyl 5-aminomethyl-2-isoxazoline-3-propionate toluene-4-sulfonate The preparation is carried out starting from (−)-menthyl 4-nitrobutyrate in analogy to Example 27. The product precipitated as the tosylate has a melting point of 142°-144° C. and is also present as an epimer mixture.

¹H-NMR: as Example 27

Example 29: 5-Aminomethyl-2-isoxazoline-3-propionic acid, racemate

The racemic product is prepared starting from tert.-butyl 4-nitrobutyrate and N-tert.-butoxycarbonylallylamine in analogy to Example 12. After cleavage of the protecting groups, it is taken up in acetone and the betaine is precipitated by adjusting the pH to 6 by means of conc. aq. ammonia. The melting point is 201° C. (with dec.).

¹H-NMR (betaine in D₂O): δ=2.48 and 2.65 (each mc, 2H, —CH₂—CH₂—), 2.85-3.45 (m, 4H, 4-H and CH₂-N), 4.8 (vb, acidic H), 4.9 (mc, 1H, 5-H).

Example 30: 5-Aminomethyl-2-isoxazoline-3-propionic acid, (−)-enantiomer a) Enantiomer resolution 80 g (0.26 mol) of the liberated base of the product from Example 27 are dissolved in 2 l of methyl ethyl ketone and 93 g (0.26 mol) of (−)-O,O'-dibenzoyl-L-tartaric acid are added, whereupon crystals slowly precipitate. After filtering off with suction, the crystals are recrystallized from the same solvent, 30 g of the salt of melting point 162° C. which is >98% enantiomerically pure according to GC analysis remaining.

b) Cleavage of the menthyl ester 20 g (0.03 mol) from a) are converted into the base by extracting from 1 N sodium hydroxide solution by shaking with tert.-butyl methyl ether. The residue which remains after concentrating is taken up in 270 ml of trifluoroacetic acid at 0° C., 3.5 ml of thioanisole and 26.5 ml of trifluoromethanesulfonic acid are added, the mixture is stirred in an ice bath for 1 hour and about 300 ml of diethyl ether are slowly added. After crystallization is complete, the residue is filtered off with suction and taken up in ethanol, and the pH is adjusted to 6.0 using conc. aq. ammonia. The betaine isolated in this way is recrystallized from water/ethanol, resulting in 2.5 g of the betaine of melting point 176° C. (dec.) which is >99% enantiomerically pure by GC.

$[\alpha]_D^{20} = -123.5°$ (c=1 in water) $^1$H-NMR (betaine in D$_2$O): as racemate

Example 31: 5-Aminomethyl-2-isoxazoline-3-propionic acid, (+)-enantiomer a) Enantiomer resolution

The mother liquid which remains from the fractional crystallization of Example 30a) is converted into the free base as described above. 66 g (0.21 mol) thereof are dissolved in ethanol and the tartrate is precipitated and recrystallized from ethanol after addition of 31.5 g (0.21 mol) of D(−)-tartaric acid. 30 g of the salt of melting point 163° C. which is >98% enantiomerically pure according to GC analysis is obtained.

b) Cleavable of the menthyl ester

The cleavage of the menthyl ester is carried out after liberating the base as described in Example 30b). 2.9 g of the betaine of melting point 183° C. (dec.) which is >99% enantiomerically pure according to GC are obtained from 20 g of tartrate after recrystallization.

$[\alpha]_D^{20} = +121°$ (c=1 in water)

Example 32: Sodium 5-acetamidomethyl-2-isoxazoline-3-carboxylate 2.5 g (0.015 mol) of the racemate from Example 29 are acetylated analogously to Example 17, resulting in 2.8 g of an amorphous product. After taking this product up in acetone, the analytically pure sodium salt can be precipitated by addition of the equivalent amount of a 10% strength acetone solution of sodium 2-ethylhexanoate. Melting point: 238° C.

$^1$H-NMR (Na salt in D$_2$O): $\delta = 1.94$ (s, 3H, Ac), 2.37 and 2.54 (each mc, 2H, —CH$_2$—CH$_2$—), 2.75 and 3.1 (AB of ABX, 2H, 4-H), 3.3 (d, J=5, 2H, CH$_2$-N), 4.7 (mc, 1H, 5-H).

Example 33: 3-(2-Carboxyethyl)-5-(2-pyridyl)-2-isoxazoline 59 g (0.38 mol) of tert.-butyl 4-nitropropionate are subjected to cycloaddition with 80 g (0.76 mol) of 2-vinylpyridine and 69.5 g (0.42 mol) of phenylene diisocyanate analogously to Example 5a). The residue which remains after working up is taken up in dichloromethane and the solution is filtered through a short column packed with celite. 77 g of an oil are obtained, which is subjected to ester cleavage and analogously to Example 12. Further purification is carried out by chromatography on silica gel using methanol/tert.-butyl methyl ether mixtures with the addition of 1% aq. ammonia. After concentrating the product fractions, a crystalline product of melting point 93° C. is obtained as the betaine by acidifying an acetone solution to pH 4 by means of trifluoroacetic acid.

$^1$H-NMR (betaine in DMSO-d$_6$): $\delta = 2.5$ (mc, 4H, —CH$_2$—CH$_2$—, 3.2 and 3.4 (AB of ABX, 2H, 4-H), 5.5 (mc, 1H, 5-H), 7.2–7.5, 7.8 and 8.55 (each m, 5 pyridyl-H).

Example 34: Methyl 3-aminomethyl-2-isoxazoline-5-propionate toluene-4-sulfonate a) Cycloaddition

For the preparation of the olefin component, 4-pentenecarboxylic acid is esterified by means of thionyl chloride and methanol according to methods known from the literature. The cycloaddition is carried out analogously to Example 5a) by means of 2-nitroethyl 2-tetrahydropyranyl ether (see V. Jäger et al., Angew. Chem. 93 (1981), 576–578). The crude product can be processed further without further purification.

b) Cleavage of the tetrahydropyranyl protecting group 200 g of the product from a) are treated overnight at room temperature with 500 ml of a 1 N methanolic hydrochloric acid. After concentrating, the mixture is chromatographed on silica gel by means of petroleum ether/tert.-butyl methyl ether.

c) Methyl 3-chloromethyl-2-isoxazoline-5-propionate 7.4 ml (0.081 mol) of phosphorus oxychloride and 33.8 ml (0.243 mol) of triethylamine are initially introduced into 200 ml of tetrahydrofuran and 5 g (0.027 mol) of the product from b), dissolved in 50 ml of tetrahydrofuran, are added dropwise at room temperature. After 20 h, the mixture is hydrolyzed with methanol and then with water, the product is extracted with dichloromethane, dried and concentrated, and the residue is purified by chromatography as under b).

d) Substitution by means of NH$_3$ 2 g from c) are dissolved in 50 ml of 2 N methanolic ammonia solution together with 100 mg of tetrabutylammonium iodide and the mixture is left at room temperature with TLC checking for 3–5 d. After completion of the reaction, the mixture is concentrated and chromatographed on silica gel (eluent: methanol/tert.-butyl methyl ether with the addition of 1% aq. NH$_3$). The tosylate can then be obtained in crystalline form from methanol/tert.-butyl methyl ether by means of 4-toluenesulfonic acid and has a melting point of 168° C.

$^1$H-NMR (tosylate in CDCl$_3$/MeOH-d$_4$ 1:1): $\delta = 1.9$ and 2.4 (each m, 2H, —CH$_2$—CH$_2$—), 2.33 (s, Tos-OH), 2.7 and 3.13 (AB of ABX, 2H, 4-H), 3.62 (s, 3H, COOMe), 3.85 (vb, 2H, CH$_2$-N), 4.7 (mc, 1H, 4-H) 7.2 and 7.7 (AA'BB', Tos-OH).

Examples 35–54

Examples 35–54 shown in Table 2b were synthesized analogously to the examples described above, and each cited in the table and characterized by the spectroscopic data.

TABLE 2b

| Example No. | Formula | notes | Analogous to Example | Melting point [°C.] | 1H-NMR [ppm] |
|---|---|---|---|---|---|
| 35 | H2N-CH2-[isoxazoline]-CH2-COOH | BOC-NH-CH2-[isoxazoline]-CH2-C(O)-OEt, H2N-CH2 | 1b-d | 137-138 | (in D2O): 2.9-3.5(m, 4H, 2CH2), 4.9-5.1(mc, 1H, 5-H) |
| 36 | H2N-CH2-[isoxazoline]-CH2-C(O)NH2 · xCF3COOH | BOC-NH-CH2-[isoxazoline]-CH2-C(O)-OEt, NH3 (Room temperature) | 3b, Cleavage: 1d | 117 | (in DMSO-d6): 2.8-3.7(m, 4H, 2CH2), 4.8-5.3(mc, 1H, 5-H), 7.7-8.8(NH2 and NH3+) |
| 37 | H2N-CH2-[isoxazoline]-CH2-C(O)-pyrrolidinyl · xHCl | BOC-NH-CH2-[isoxazoline]-CH2-C(O)-OEt, HN-pyrrolidine (reflux) | 3b, Cleavage: 1d | 147-148 | (in DMSO-d6): 1.6-2.0(m, 4H, 2CH2), 2.9-3.8(m, 8H, 4CH2), 4.8-5.35(mc, 1H, 5-H) 8.5-9.0 (acidic H) |
| 38 | H2N-CH2-[isoxazoline]-CH2-C(O)-morpholinyl · xHCl | BOC-NH-CH2-[isoxazoline]-CH2-C(O)-OEt, HN-morpholine | 3b, Cleavage: 1d | 171-173 | (in DMSO-d6): 2.8-3.75(m, 12H, 6CH2), 4.7-5.2(mc, 1H, 5-H), 8.2-8.5 (acidic H) |
| 39 | H2N-CH2-[isoxazoline]-CH2-C(O)-N(CH3)2 · xHCl | BOC-NH-CH2-[isoxazoline]-CH2-C(O)-OEt, HN(CH3)2 | 3b, Cleavage: 1d | 142 | (in DMSO-d6): 2.9 und 3.05(each. sb, 3H, 2CH3) ca. 2.8-3.5(m, 4H, 2CH2), 4.65-5.15(mc. 1H, 5-H) 8.25-8.7 (acidic H) |
| 40 | HO-CH2-[pyridyl-isoxazoline]-CH2OH | O2N-CH2-[pyridyl-isoxazoline]-CH2-O-tBu | 25a,b | 133.6 | (in D2O): 3.0-4.05 (AB of ABX, 2H, 4-H), 5.7-6.05 (X v. ABX, 1H, 5-H), 4.35 (vb, 2H, CH2—O), 7.5-8.6(m, 4 Aryl-H) |
| 41a | CH3-CH(Ph)-NH-C(O)-[isoxazoline]-CH2-NH2 · xCF3COOH | BOC-NH-CH2-[isoxazoline]-CH2-C(O)-OEt, H2N-CH(CH3)Ph | 3b, Cleavage: 1d | 122 [α]D20 = −104.2° c = 1, H2O | (in DMSO-d6): identical for both epimers Epimere 1.5(d, J=7.2, 3H, CH3), 2.95-3.5(m, 2CH2), 4.8-5.15(m, 2H, CHN and CHO), 7.1-7.5(m, 5 Aryl-H), 8.1(NH3+), 9.0d, J=8.7, NH) |

TABLE 2b-continued

| Example No. | Formula | notes | Analogous to Example | Melting point [°C.] | ¹H-NMR [ppm] |
|---|---|---|---|---|---|
| 41b | | The diastereomers were obtained separately by fractional crystallization from ethyl acetate/petroleum ether | 134 ([α]$_D^{20}$ = +48.4°, c = 1, H$_2$O) | | |
| 42 | | | 25a,b | 67 | (in DMSO-d$_6$): 2.8–3.3(acidic H) 3.7 and 4.3(each, s, 2H, 2CH$_2$) 6.1(s, 1H, 4-H) |
| 43 | | | 25a,b | 127 | (in DMSO-d$_6$): 2.7(s, 6H, NMe$_2$), 4.4–4.45(each, s, 2H, 2CH$_2$) 6.7(s, 1H, 4-H) |
| 44 | | | 1a–d | 174 | (in DMSO-d$_6$): 1.65(vb, 6H, 2Me), 6.8(s, 1H, 4-H), 8.5–8.85(acidic H) |
| 45 | | | CA, cleavage: 25a–d methylation: 18 | 86 | (in DMSO-d$_6$): 3.1(s, 9H, NMe$_3$), 4.4d, J=6, 2H, CH$_2$OH), 4.8(s, 2H, CH$_2$N), 5.3(t, J=6, OH), 6.7(s, 1H, 4-H) |
| 46 | | Methylation in Aceton/Methanol/water 2:2:1 | 1b–d Methylation: 18 | 202 | (in D$_2$O): 2.52 u. 2.95 each t j=7, 2H, —CH$_2$—CH$_2$—) 3.17(s, 9H, NMe$_3$$^+$), 4.7(s, 2H, —CH$_2$—N$^+$), 6.77(s, 1H, 4-H) |
| 47 | | | cyclo addition and substitution: 3a,b cleavage: 1d | 132–134 | (in DMSO-d$_6$): 1.5–1.9(m, 6H, 3CH$_2$) 2.6a and 2.9(each. t, J=7, 2H, —CH—CH—) 3.2–3.6(m, 4H, 2CH$_2$—N) 4.5(sb, 2H, CH$_2$—N), 6.75(s, 1H, 4-H) |

TABLE 2b-continued

| Example No. | Formula | notes | Analogous to Example | Melting point [°C.] | 1H-NMR [ppm] |
|---|---|---|---|---|---|
| 48 | [structure: H2N-CH2-isoxazole-CH=C-CH2-P(O)(OMe)2, xHCl] | BOC-N(H)-CH2-C≡CH, O2N-P(OMe)2 | 5a, 1d | 127/dec | (in DMSO-d6): 2.0–2.3 and 2.7–2.9(each. m, 2H, —CH2—CH2—), 3.65(d, J=10.8, 6H, 2 OMe), 4.2(s, 2H, CH2—N), 6.7(s, 1H, 4-H), 8.95(acidic H) |
| 49 | [structure: H2N-CH2-isoxazole-CH=C-CH2-P(CH)2, xHBr] | Beispiel 48 | 16 | from 200 dec. | (in D2O/NaOD): 1.55–1.8 and 2.75–2.9(each. mc, 2H, —CH2—CH2—), 4.2(s, 2H, CH2—N), 6.43(s, 1H, 4-H) |
| 50 | [structure: H2N-CH2-isoxazole-CH=C-CH2-C(O)NH2, xHCl] | BOC-N(H)-CH2-isoxazole-CH=C-CH2-C(O)OH, NH3 | 24b cleavage: 1d | 238–239 | (in DMSO-d6): 2.44 and 2.84(each. t, 2H, —CH2—CH2—), 4.2(s, 2H, CH2—N), 6.55(s, 1H, 4-H), 6.9 and 7.5(each.sb, —1H, COHN2), 8.9(NH3+) |
| 51 | [structure with phenylalanine and glycine amide on isoxazole, xCF3COOH] | [structure with OH, HN-BOC, phenyl] | Peptide:24b Debenzylation: 24c Boc cleavage: 24d | 117–122 | (in CDCl3/MeOH-d4 1:1): 2.6 and 2.93(each mc, 2H, —CH2—CH2—), 3.1(mc, 2H, Ph—CH2), 3.9(sb, 2H, —CH2—COOH) 4.1(t, J=7.5, 1H, CHN), 4.4(sb, 2H, CH2—N), 6.0(s, 1H, 4-H), 7.1–7.4(m, 5-Aryl-H) |
| 52 | [structure: H2C=... -C(O)N(H)-...-isoxazole-CH=C-CH2-C(O)OH] | [structure: H2C=...-C(O)Cl, benzyl ester] Acylation similar to 17 Debenzylation: 24c | | 115 | (in MeOH-d4): 2.65 and 2.92(each. t, 2H, J=7, —CH2—CH2—CH2—), 4.5(sb, 2H, CH2—N, 5.6–5.75(m, 1H, =CH—) 6.1(s, 1H, 4-H) 6.15–6.3(m, 2H, =CH2) |
| 53 | [structure: O2N-CH2-isoxazole-CH=C-CH2-C(O)OH with O=C-N(H)-CH2-CH2-CH2- and benzyl ester] | [structure with benzyl ester], O2N—CH3 | see above note for Example 5 | 98–100 | (in CDCl3/MeOH-d4 1:1): 2.2–2.4(m, 4H, CH2—CH2—) 2.65 and 2.92(each t, J=7, 2H, —CH2—CH2—), 4.4(s, 2H, CH2—N), 4.5(t, 2H, O2NCH2) 6.1(s, 1H, 4-H) |

TABLE 2b-continued

| Example No. | Formula | notes | Analogous to Example | Melting point [°C] | ¹H-NMR [ppm] |
|---|---|---|---|---|---|
| 54 | [structure: H₂N-CH₂-C(=N-O-)-CH=C-CH₂-C(=O)-OMe, oxalate] | [structure: HC≡C-...-C(=O)-OMe with NO₂ and tetrahydropyranyloxyethyl] | 34a-c | 175 | (in MeOH-d4): 2.77 and 3.1(each. t, J=7, 2H, —CH₂—CH₂—) 3.68(s, 3H, CH₃—) 4.2(s, 2H, CH₂—N) 6.3(s, 1H, 4-H) |
| 55 | [structure: HO-N=C(H)-...-C(=O)-OMe] | [structure: HC≡C-C(=NOH)-C(Cl)=N-OH with OMe ester] | 1b | 99 | (in CDCl₃): 2.75 und 3.1 (jew.t, J=7, 2H, —CH₂—CH₂); 3.7(s, 3H, OMe); 6.4(s, 1H, 4-H); 8.2(s, 1H, Oxim-CH); 9.3(sb, 1H, Oxim-OH) |
| 56 | [structure: HO-C(=O)-...-C(=N-O-)-C(=O)-OH] | [structure: acrylate with glycine ethyl ester] | 1b,c (Überschuß NaOH) | 135 | (in DMSO-d6): 2.9–3.6(AB von ABX, 2H, 4-H) 4.9-5.25(X von ABX, 1H, 5-H) |
| 57 | [structure: menthyl ester with dicyclohexylammonium salt] | [structure: acrylate menthyl ester with glycine] | 1b,c | 103 | (in CDCl₃): 0.7(d, 3H, J=7, CH₃) 0.8–2.15(m, 35H, 2CH₃, 13CH₂, 3CH) 3.1(mc, 2H, 2CHN) 3.3–3.65(AB von ABX, 2H, 4-H) 4.75(mc, 1H, Menthyl-CHO) 5.05(X von ABX, 1H, 5-H) |
| 58 | [structure: Me₃N⁺-CH₂-...-C(=O)-O-trimethylcyclohexyl, I⁻] | Example 9 | 18 | 158 | (in MeOH-d4): 0.70–2.0(m, 16H, 3CH₃, 3CH₂, 1CH) 2.72 und 3.05(jew.mc, 2H, —CH₂—CH₂), 2H, 3.22(s, 9H, NMe₃) 4.8–5.0(m, CHO, CH₂—N und HDO) 6.82(s, 1H, 4-H) |

Example 59: 5-Hydroxylmethyl-isoxazole-3-propionate sodium salt a) Propargylalcohol-tert.-butylether 101 ml (1.9 mol) propargylalcohol are dissolved at 0° C. in about 1 l dichloromethan in a pressure bottle, 20 ml of concentrated sulfuric acid and 450 g (8 mol) isobuten are added. After 5 hours at 0° C. excess isobuten is removed, washed with a sodiumcarbonate solution, dried, concentrated and finally the product is distilled.

b) Cycoloaddition with benzylnitrobutyrate 33.7 g (0.3 mol) of the product obtained under a) are treated analogously to Example 5 with 66.9 g (0.3 mol) of benzyl nitrobutyrate, 0.35 mol of phenylene diisocyanate and triethylamine. The crude product can be purified by chromatography on silica gel eluent. ethylacetate/petroleum ether 1:1.

c) Removal of tert.-butylether protecting group 100 g of the crude product obtained under b) are dissolved in 1.5 l dichloromethan and 300 ml trifluoracetic acid. Completion of reaction is followed by TLC checking. After concentration the crude product is purified by chromatography on silica gel (eluent: ethylacetate/petroleum ether 1:1) and an oily product is obtained.

d) Hydrolysis of the benzylic acid ester 2 g (0.0077 mol) of the product obtained under c) are dissolved in 10 ml of ethanol, 10 ml of 1 N NaOY is added and is stirred until completion of the reaction (TLC-checking). The product is precipitated by addition of acetone and recrystallized several times from methanol/tert.-butyl-methyl ether. Melting point: 168° C.

$^1$H-NMR(D$_2$O): δ=2.45 and 2.85 (jew.t, 2H, —CH$_2$—Ch$_2$—), 4.6 (s, 2H, CH$_2$-O), 6.26 (s, 1H, 4-H).

The compounds of the formula I were investigated in the following experimental test arrangements, which are recognized as being particularly suitable for the evaluation of the quality of action of compounds of this type which are active in the CNS, to characterize their valuable neuoprotective properties and good tolerability.

1. "High affinity" absorption of $^3$H-aspartate in a vesicle preparation from rat brain.

Test principle: Fresh synaptic vesicles (synaptosomes) from rat cortex are incubated with buffer solution and $^3$H-D-aspartate and $^3$H-D-aspartate in the vesicles is measured. Preparations which in comparison to control synaptosomes increase the high affinity $^3$H-D-aspartate absorption and those which prevent the loss of $^3$H-D-aspartate by reliberation are regarded as particularly interesting.

Experimental protocol: The experiments for $^3$H-D-aspartate absorption were carried out by the method of Anand et al. (Biochem. Pharmacol., 35 (1986), 1055-1057). The synaptic vesicles were dissected out of cerebral cortex from male Sprague-Dawley rats. The preparations were tested at four concentrations as double samples in parallel with control samples containing buffer. The incubation medium (pH 7.4) contains: 1.2 mM KH$_2$PO$_4$, 5 mM KCl, 5 mM pyruvate, 1.2 mM glucose, 1.2 mM MgCl$_2$, 114 mM NaCl, 25 mM NaHCO$_3$. For the non-specific $^3$H-D-aspartate absorption, NaCl was replaced by 114 mM choline chloride and NaHCO$_3$ by 25 mM KHCO$_3$. An aliquot of the vesicle suspension (about 25 μg/ml of test solution) was added to the test sample which was temperature controlled at 37° C. and aerated with Carbogen (5% CO$_2$, 95% O$_2$) and preincubated for 2 minutes. The three minutes incubation for the amino acid absorption was started by addition of 50 μl of $^3$H-D-aspartate (specific activity 25 Ci/mmol, 10 pmol/ml of test solution). The vesicles were separated from the incubation medium by filtration and additional washing of the adhering labeled amino acids using a Titertek cell harvester (Flow Laboratories, Meckenheim). The $^3$H-D-aspartate absorption was measured by means of a liquid scintillation counter (Canberra-Packard, Model 1500, Frankfurt).

The preparation activity is indicated in percent of the specific $^3$H-D-aspartate absorption, relative to control values (100%), in Table 3. Adenosine triphosphate (ATP) was used for comparison as the standard substance (see Table 3) and at 1 mM caused a 35% increase in the $^3$H-D-aspartate absorption. ATP is inactive at a lower concentration than 500 μm, but shows a concentration-dependent action at a higher concentration.

TABLE 3

| Example No. | Stimulation of the absorption Preparation concentration μM | $^3$H-D-aspartate Stimulation (%) |
|---|---|---|
| 1. | 500 | 15 |
| 2. | 500 | 12 |
| 3. | 500 | 20 |
| 5. | 10 | 26 |
| 6. | 10 | 17 |
| 8. | 10 | 13 |
| 9. | 100 | 19 |
| 10. | 500 | 23 |
| 12. | 500 | 17 |
| 13. | 500 | 33 |
| 14. | 500 | 19 |
| 16. | 1000 | 19 |
| 18. | 100 | 46 |
| 19. | 100 | 25 |
| 22. | 100 | 23 |
| 24. | 500 | 28 |
| 25. | 500 | 20 |
| 31. | 500 | 21 |
| 32. | 100 | 19 |
| 39. | 1000 | 14 |
| 50. | 500 | 15 |
| 56. | 500 | 17 |
| 58. | 10 | 35 |
| ATP | 500 | 31 |
| ATP | 1000 | 35 |
| ATP | 2000 | 57 |
| ATP | 5000 | 121 |

2. Inhibition of $^3$H-acetylcholine release from striatum sections of the rat brain Test principle: For the test, fresh striatum sections from rat brain were rinsed with buffer solution in a special chamber and the release of the tritium-labeled acetylcholine was measured after stimulation with NMDA. Preparations having NMDA-antagonist action inhibit acetylcholine release.

Experimental protocol: The superfusion experiments were carried out by the method of Wichman et al. (Naunyn-Schmied. Arch. Pharmacol., 338 (1988), 623-631). Rat brain sections, 0.5 mm thick, were preincubated for 30 min in 2 ml of incubation medium which contains 0.1 μmol/l of $^3$H-choline having a specific activity of 80 Ci/mmol. In each of 6 superfusion chambers, a section was transferred and superfused for 90 min at a rate of 1.5 ml/min. 2 min fraction of the superfusate were continuously collected. Each section was superfused twice with 25 μmol/l of NMDA of two minutes each time in order to stimulate the release of acetylcholine. The first stimulus (S$_1$) takes place between the 54th and the 56th minute and the 2nd stimulus (S$_2$) between the 76th and 78th minute. The incubation medium contained, in mmol/l: NaCl 118, KCl 4.8, CaCl$_2$ 1.2, MgSO$_4$ 1.2, NaHCO$_3$ 25, KH$_2$PO$_4$ 1.2 and glucose 10. The medium was saturated with Carbogen at 37° C. The pH was adjusted to 7.4 NMDA and the novel preparations to be tested were dissolved in superfusion medium. The superfusion was carried out using Mg$^{2+}$-free medium. Tritium from the dissolved sections and from the superfusate was determined by liquid scintillation counting using a Packard ® 1900 CA (Frankfurt) at a 50% efficiency.

Calculation of the Results

Basal release and NMDA-stimulated release for S$_1$ and S$_2$ were expressed in %/min of each fraction (Limberger et al, Naunyn Schmied. Arch. Pharmacol. 339 (1988), 53–61).

The value for the stimulated release S$_2$/S$_1$ was calculated for the control as 0.69±0.09. The value decreases if a substance, such as, for example, the NMDA receptor antagonist CPP (3-(+)-2-carboxypiperazin-4-ylpropyl-1-phosphonic acid) known from the literature inhibited the NMDA-stimulated release. The inhibition of the stimulated release by preparations was calculated in percent, relative to the control value, and is indicated in Table 4.

TABLE 4

| Inhibition of $^3$H-acetylcholine release from striatum sections | | |
|---|---|---|
| Example No. | Preparation concentration μM | Inhibition (%) |
| 1. | 10 | 13 |
| 7. | 10 | 28 |
| 8. | 10 | 30 |
| 18. | 10 | 22 |
| 19. | 10 | 16 |
| 20. | 10 | 18 |
| 21. | 10 | 20 |
| 22. | 10 | 15 |
| 33. | 10 | 26 |
| 34. | 10 | 9 |
| 56. | 10 | 11 |
| 59. | 10 | 26 |
| CPP | 10 | 30 |

3. Inhibition of $^3$H-MK-801 binding to membranes from rat brain

Test principle: MK-801 is a non-competitive antagonist which binds to ion channels coupled to NMDA receptors (Yoneda et al., Brain Res. 499 (1989), 305). Membranes from whole brain containing preparation and $^3$H-MK-801 are incubated in the test. The binding of $^3$H-MK-801 or its displacement by preparations (antagonists) is determined by radiochemical methods.

Experimental protocol: The binding experiments are carried out by the method of Reynolds et al. (Proc. Natl. Acad. Sci. USA, 84 (1987), 7744). Membrane preparation is first carried out according to Reynolds. Test samples are then pipetted, buffer and test preparation being initially introduced, then preincubated with protein for 2 minutes, and initiated using $^3$H-MK801. The membranes are thawed at 37° C., incubated at 37° C. for 10 minutes and homogenized for 15 seconds at half the maximum speed by means of a Polytron, then used in the cool state again. The incubation medium contains: pH 7.4 Hepes buffer 20 mM, preparations in three concentrations 5 μM, 10 μM and 50 μM, membranes 500 μg/ml of test solution, $^3$H-MK801 1 nM. Incubation is carried out at room temperature (23° C.) for 60 minutes and is then stopped by filtration. For this purpose, glass fiber paper No. 32 from Schleicher and Schüll, which had been soaked in 0.03% polyethyleneimine for 30 minutes on the day before the experiment are counted in 4 ml of "Packard 199 TM" Scintillation fluid (Frankfurt). Tritium is determined by liquid scintillation counting using a Packard 1500.

Calculation of the results: The calculation of the binding in femtomol/mg of protein over a period of 60 min. was carried out using a small calculator (HP-97). If a substance antagonizes the binding, the value decreases. Substance activities are indicated in Table 5 as percentages, i.e. in % binding compared to the control. The activity of the comparison preparation CPP (3-(+)-2-carboxypiperazin-4-ylpropyl-1-phosphonic acid) at 5 μM, 10 μM and 50 μM is always determined to check the test.

TABLE 5

| Inhibition of $^3$H-MK-801 binding to the NMDA receptor-channel complex | | |
|---|---|---|
| Example No. | Preparation concentration μM | inhibition (%) |
| 2. | 50 | 10 |
| 5. | 50 | 78 |
| 19. | 50 | 16 |
| 21. | 50 | 45 |
| 57. | 50 | 43 |
| CPP | 50 | 81 |

4. Inhibition of NMDA-induced-cramps in the mouse

The examples listed below show neuroprotective activity in that they antagonize the cramps induced by NMDA (N-methyl-(D)-aspartate). To this end, intravenous injections of 20–30 mg/kg of NMDA are carried out on a male NMRI (Naval Medical Research Institute) mice of 22–24 g body weight, which leads to stereotypes, clonic cramps and in the majority of cases to mortality. In order to investigate an NMDA-antagonist activity of the test substances, they are administered orally one hour before NMDA. The animals are then observed for the abovementioned symptoms for up to 60 min. The number of animals with clonic cramps and the incidence of mortality, expressed in percent change compared to the control group, is regarded as the evaluation criterion. The GABA agonist muscimol known from the literature and the substance MK 801 described as an NMDA antagonist, which are also described as an NMDA antagonist, which are also described as active against neurodegenerative changes, are used as comparison preparations.

As the examples investigated show considerable differences in toxicity compared to the standard substances, the LD$_{50}$ values are also listed in Table 6,

TABLE 6

| Inhibition of NMDA-induced convulsions and toxicity in the mouse | | | | |
|---|---|---|---|---|
| Example No. | Dose [mg/kg] | Inhibition of convulsions | Inhibition of mortality | LD$_{50}$ [mg/kg] |
| Muscimol | 0.3 p.o. | 40% | 60% | 3–10 i.v. |
| MK 801 | 0.3 p.o. | 60% | 60% | 30–60 i.v. |
| 1 | 63 p.o. | 50% | 50% | >200 i.v. |

TABLE 6-continued

Inhibition of NMDA-induced convulsions and toxicity in the mouse

| Example No. | Dose [mg/kg] | Inhibition of convulsions | Inhibition of mortality | $LD_{50}$ [mg/kg] |
|---|---|---|---|---|
| 6 | 50 p.o. | 20% | 40% | >100 i.v. |
| 8 | 50 p.o. | 70% | 100% | 50–100 i.v. |
| 10 | 50 p.o. | 10% | 70% | >100 i.v. |
| 12 | 50 p.o. | 45% | 60% | >100 i.v. |
| 14 | 50 p.o. | 40% | 40% | >300 i.p. |
| 15 | 50 p.o. | 40% | 100% | >100 i.v. |
| 16 | 50 p.o. | 30% | 30% | — |
| 17 | 30 p.o. | 30% | 100% | >300 i.p. |
| 20 | 50 p.o. | 10% | 100% | 25–50 i.v. |
| 21 | 50 p.o. | 30% | 40% | 25–50 i.v. |
| 23 | 50 p.o. | 40% | 40% | >300 i.p. |
| 26 | 50 p.o. | 40% | +/−0% | >100 i.v. |
| 27 | 50 p.o. | 20% | 20% | 50–100 i.v. |
| 28 | 50 p.o. | 20% | 20% | — |
| 29 | 50 p.o. | 20% | 20% | >200 i.v. |
| 32 | 50 p.o. | 30% | 50% | >100 i.v. |
| 53 | 50 p.o. | 33% | 33% | — |
| 55 | 50 p.o. | 33% | 100% | — |

5. Neuroprotection after forebrain ischemia in the gerbil

Following the experimental procedure described below and published elsewhere (K. Rudolphi et al., J. Cereb. Blood Flow Metabl., 7:74, 1987), it turns out that the examples listed below are able to protect cerebral nerve cells against severe ischemic damage.

A 5-minutes' ischemia of the forebrain with subsequent recirculation is produced in 20 male Mongolian gerbils under halothane anesthesia by bilateral closure of the corotid artery by means of aneurysm clips. 7 days later, the animals are decapitated under halothane anesthesia, the brains are fixed by immersion in Carnoy solution and the extent of neuron damage in the $CA_1$ region of the hippocampus is determined "blind" with the aid of a 5-stage histopathological score. The test substance is administered intraperitoneally or orally 15 minutes before ischemia to each group of 10 gerbils. One ischemic control group, also of 10 animals, is treated with the respective solvents per test substance. The results are summarized in Table 7 as the % change of the mean neurological behavior score or histopathological score (sum of the individual scores/number of animals) of the treated group versus the control group.

TABLE 7

Necroses of the $CA_1$ pyramidal cells after three minutes' forebrain ischemia in the Mongolian gerbil

| Example No. | Dose (mg/kg) | Cell necroses (% change) | Behavior score (% change) |
|---|---|---|---|
| Muscimol | 5 i.p. | −74 | +41 |
| MK 801 | 5 i.p. | −23 | +24 |
| 8 | 50 p.o. | −46 | 0 |
| 12 | 10 i.p. | −32 | 0 |
| 12 | 50 p.o. | −14 | 0 |
| 16 | 50 p.o. | −27 | 0 |
| 18 | 50 p.o. | −23 | +15 |
| 19 | 50 p.o. | −25 | 0 |

It can be seen from the compilation that the standard substances muscimol and MK 801 admittedly also lead to a reduction in the dying cells, but show distinctly more negative post-ischemic symptoms in the behavior score, while the test substances do not negatively adversely affect the neurological symptoms.

6. The photochemically-induced infarct of the forebrain of the rat can be tested as follows The theoretical basis and practical application of this method has already been described earlier (Grome et al., J. Cereb. Blood Flow Metabol. 8 (1988) 89-95). Male Sprague-Dawley rats (300–350 g) are anesthetized with 1% halothane in oxygen. A small cut is made in the scalp and 1 ml of the photochemically active dye Bengal Rose (5 mg/ml in sodium chloride solution) is administered i.v. A part of the skull (diameter of 3 mm) is then illuminated with green light (570 nm) from a xenon lamp (75 W) for 15 minutes. At this point, the anesthesia is terminated and the rats are divided randomly into medicament- and placebo-treated groups (n=6). In the experiments in which only one dose of the substance is administered, administration takes place 30 minutes after induction of ischemia. 24 hours later, these animals are sacrificed by decapitation. The brains are rapidly removed and frozen. Serial cryostat sections through the entire extent of the lesion are stained using Cresyl Violet. 90 of these sections are measured by means of an image analysis system to determine the volume of the destruction caused by ischemia. The volume is calculated in microliters and expressed as the percentage change relative to the placebo-treated control. In the two hours following the ischemic events, the animals are observed intensively and a behavior score having a scale from 0 (no symptoms) to 4 (severe motor symptoms including difficulties in the ingestion of food) is prepared.

We claim:

1. A compound of the formula Ia, Ib or Ic

(Ia)

(Ib)

(Ic)

in which
$R^1$ is a radical of the formula IIa or IIb

(IIa)

(IIb)

in which
$R^3$ and $R^4$ independently of one another are hydrogen or $C_1$–$C_4$-alkyl;
$R^5$ in formula IIa is a free electron pair;

$R^5$ in formula IIb is hydrogen, $(C_1-C_4)$-alkyl or $(C_3-C_6)$-cycloalkyl;

$R^6$ and $R^7$ independently of one another are hydrogen; $C_1-C_6$-alkyl; $C_3-C_6$-cycloalkyl; $C_6-C_{12}$-aryl-$C_1-C_4$-alkyl; carbamimidoyl; $C_1-C_6$-alkylcarbonyl, $C_1-C_4$-alkenylcarbonyl, $C_1-C_6$-alkyloxycarbonyl, $C_6-C_{12}$-aryl-$C_1-C_4$-alkylcarbonyl, $C_6-C_{10}$-aryl-$C_1-C_4$-alkyloxycarbonyl, $C_6-C_{10}$-arylcarbonyl, or the radical of a naturally occurring α-amino acid or γ-aminobutyric acid which can be substituted by $C_1-C_6$-alkyl, hydroxyl, halogen, amino or nitro, which radical is bonded to the nitrogen of the formula IIa or b by an amide binding; or $R^5$, $R^6$ and $R^7$ in formula IIb independently of one another are $C_1-C_4$-alkyl or $C_3-C_6$-cycloalkyl;

$An^-$ is an anion radical of a physiologically acceptable salt, or an internal anionic radical when the compound is a zwitterion.

$R^2$ is a radical of the formula II $$-(CH_2)_n-X \quad (III)$$

in which n is 0 or an integer from 1 to 4:

X is hydroxyl; $C_1-C_4$-alkyloxy; carboxyl; haloformyl; $C_1-C_{12}$-alkyloxycarbonyl; benzyloxycarbonyl, $C_3-C_6$-cycloalkyloxycarbonyl, or said benzyloxycarbonyl or $C_3-C_6$-cycloalkyloxycarbonyl which is monosubstituted or polysubstituted by $C_1-C_6$-alkyl, or X is carbonyl which is linked by a peptide bond to a naturally occurring α-amino acid, γ-aminobutyric acid or a naturally occurring dipeptide, or X is aminocarbonyl in which amino can be mono- or disubstituted by $C_1-C_6$-alkyl or monosubstituted by phenyl-$C_1-C_6$-alkyl; and A is a C,C-single or a C,C-double bond;

with the proviso that n is from 2 to 4 if X is hydroxyl or $C_1-C_4$-alkyloxy, or its stereoisomer or its physiologically acceptable salt.

2. A compound of the formula Ia or Ib as claimed in claim 1, in which $R^1$ is a radical of the formula IIa or IIb as claimed in claim 1, in which $R^3$ and $R^4$ independently of one another are hydrogen or $C_1-C_4$-alkyl;

$R^5$ in formula IIa is a free electron pair or;

$R^5$ in formula IIb is hydrogen, $(C_1-C_4)$-alkyl or $(C_3-C_6)$-cycloalkyl;

$R^6$ and $R^7$ independently of one another are hydrogen; $C_1-C_4$-alkyl; or phenyl -$C_1-C_2$-alkyl; or $R^6$ is hydrogen and $R^7$ is a carbamimidoyl; $C_1-C_6$-alkylcarbonyl, $C_1-C_4$-alkenylcarbonyl, $C_1-C_6$-alkyloxycarbonyl, phenyl-$C_1-C_4$-alkylcarbonyl, benzyloxycarbonyl, benzoyl, or the radical of a naturally occurring α-amino acid or γ-aminobutyric acid, which can be substituted by $C_1-C_4$-alkyl, hydroxyl, halogen, amino or nitro, which radical is bonded to the nitrogen of the formula II by an amide binding; or $R^5$, $R^6$ and $R^7$ in formula IIb independently of one another are $C_1-C_4$-alkyl or $C_3-C_6$-cycloalkyl;

$R^2$ is a radical of the formula III as claimed in claim 1, in which n is 0 or an integer from 1 to 3;

X is hydroxyl; $C_1-C_4$-alkyloxy; carboxyl; $C_1-C_4$-alkyloxycarbonyl; benzyloxycarbonyl, $C_3-C_6$-cycloalkylooxycarbonyl or said benzyloxycarbonyl or $C_3-C_6$-cycloalkyloxycarbonyl which is mono- or polysubstituted by $C_1-C_6$-alkyl; or X is a carbonyl which is linked by a peptide bond to a naturally occurring α-amino acid, γ-aminobutyric acid or a naturally occurring dipeptide; or X is aminocarbonyl in which amino can be mono- or disubstituted by $C_1-C_4$-alkyl or monosubstituted by phenyl-$C_1-C_4$-alkyl; and A is a C,C-single or a C,C-double bond.

3. A compound of the formula Ia as claimed in claim 1, in which $R^1$ is a radical of the formula IIa or IIb as claimed in claim 1, in which $R^3$ and $R^4$ independently of one another are hydrogen or $C_1-C_4$-alkyl;

$R^5$ in formula IIa is a free electron pair;

$R^5$ in formula IIb is hydrogen, $(C_1-C_4)$-alkyl or $(C_3-C_6)$-cycloalkyl;

$R^6$ and $R^7$ independently of one another are hydrogen; $C_1-C_4$-alkyl; or phenyl-$C_1-C_2$-alkyl; or $R^6$ is hydrogen and $R^7$ is carbamimidoyl, $C_1-C_6$-alkylcarbonyl, or the radical of a naturally occurring α-amino acid or γ-aminobutyric acid, which radical is bonded to the nitrogen of the formula II by an amide binding; or $R^5$, $R^6$ and $R^7$ in formula IIb are $C_1-C_4$-alkyl;

$R^2$ is a radical of the formula III as claimed in claim 1, in which n is 0 or an integer from 1 to 4;

X is hydroxyl; $C_1-C_4$-alkyloxy; carboxyl; haloformyl; $C_1-C_4$-alkyloxycarbonyl; benzyloxycarbonyl, $C_3-C_6$-cycloalyloxycarbonyl or said benzyloxycarbonyl or $C_3-C_6$-cycloalkyloxy-carbonyl which is mono- or polysubstituted by $C_1-C_6$-alkyl; or X is carbonyl which can be linked by a peptide bond to a naturally occurring α-amino acid or γ-aminobutyric acid; or X is aminocarbonyl in which amino is mono- or disubstituted by $C_1-C_4$-alkyl, and A is a C,C-single or a C,C-double bond;

with the proviso that A is not a C,C double bond if X is OH and N=0.

4. A compound of the formula Ia as claimed in claim 1, in which $R^1$ is a radical of the formula IIa or IIb as claimed in claim 1, in which $R^3$ and $R^4$ independently of one another are hydrogen or $C_1-C_4$-alkyl;

$R^5$ in formula IIa is a free electron pair;

$R^5$ in formula IIb is hydrogen, $(C_1-C_4)$-alkyl or $(C_3-C_6)$-cycloalkyl;

$R^6$ and $R^7$ independently of one another are hydrogen; $C_1-C_4$-alkyl; or benzyl; or $R^6$ is hydrogen and $R^7$ is a carbamimidoyl; $C_1-C_6$-alkylcarbonyl, or the radical of a naturally occurring α-amino acid, which radical is bonded to the nitrogen of the formula II by an amide binding; or $R^5$, $R^6$ and $R^7$ in formula IIb are $C_1-C_4$-alkyl;

$R^2$ is a radical of the formula III as claimed in claim 1, in which n is 0, 1 or 2;

X is hydroxyl; carboxyl; $C_1-C_4$-alkyloxy; benzyloxycarbonyl, cyclohexyloxycarbonyl or said benzyloxycarbonyl or cyclohexyloxycarbonyl which is mono- or polysubstituted by $C_1-C_6$-alkyl; or X is carbonyl which can be linked by a peptide bond to a naturally occurring α-amino acid; and A is a C,C-single or a C,C-double bond;

with the proviso that A is not a C,C double bond, if X is OH and n is O.

5. A compound of the formula Ib as claimed in claim 1, in which
R¹ is a radical of the formula IIa or IIb as claimed in claim 1, in which
R³ and R⁴ are hydrogen;
R⁵ in formula IIa is a free electron pair;
R⁵ in formula IIb is hydrogen, $(C_1-C_4)$-alkyl or $(C_3-C_6)$-cycloalkyl;
R⁶ and R⁷ independently of one another are hydrogen; $C_1-C_4$-alkyl; or phenyl-$C_1-C_2$-alkyl; or
R⁶ is hydrogen and R⁷ is $C_1-C_4$-acyl; $C_1-C_6$-alkylcarbonyl, benzoyl or the radical of a naturally occurring α-amino acid or γ-aminobutyric acid, which radical is bonded to the nitrogen of the formula II by an amide binding; or
R⁵, R⁶ and R⁷ in formula IIb independently of one another are $C_1-C_4$-alkyl or $C_3-C_6$-cycloalkyl;
R² is a radical of the formula III as claimed in claim 1, in which
n is 0, 1 or 2;
X is carboxyl; haloformyl; $C_1-C_4$-alkyloxycarbonyl; benzyloxycarbonyl, $C_3-C_6$-cycloalkylcarbonyl or said benzyloxycarbonyl or $C_3-C_6$-cycloalkylcarbonyl which is mono- or polysubstituted by $C_1-C_6$-alkyl; or X is carbonyl which is linked by a peptide bond to a naturally occurring α-amino acid or γ-aminobutyric acid; or X is aminocarbonyl in which amino can be mono- or disubstituted by $C_1-C_4$-alkyl; and
A is a C,C-single or a C,C-double bond.

6. A compound of the formula Ib as claimed in claim 1, in which
R¹ is a radical of the formula IIa or IIb as claimed in claim 1, in which
R³ and R⁴ are hydrogen;
R⁵ in formula IIa is a free electron pair;
R⁵ in formula IIb is hydrogen, $(C_1-C_4)$-alkyl or $(C_3-C_6)$-cycloalkyl;
R⁶ and R⁷ independently of one another are hydrogen or $C_1-C_4$-alkyl; or
R⁶ is hydrogen and R⁷ is $C_1-C_6$-alkylcarbonyl; or
R⁵, R⁶ and R⁷ in formula IIb are $C_1-C_4$-alkyl;
R² is a radical of the formula III as claimed in claim 1, in which
n is 2 and
X is carboxyl, $C_1-C_4$-alkyloxycarbonyl; benzyloxycarbonyl; cyclohexylcarbonyl or cyclohexylcarbonyl which is mono- or polysubstituted by $C_1-C_6$-alkyl; or X is carbonyl which is linked by a peptide bond to a naturally occurring α-amino acid; and
A is a C,C-single or a C,C-double bond.

7. A compound of the formula Ia as claimed in claim 1, in which A is a C,C-double bond.

8. A compound of the formula Ia, Ib or Ic as claimed in claim 1, selected from the group consisting of:
benzyl 5-aminomethylisoxazole-3-propionate hydrochloride,
ethyl 5-aminomethylisoxazole-3-propionate hydrochloride,
(+)-methyl 5-aminomethylisoxazole-3-propionate toluene-4-sulfonate,
(−)-menthyl 5-aminomethylisoxazole-3-propionate toluene-4-sulfonate,
cis-(3,3,5)trimethylcyclohexyl 5-aminomethylisoxazole-3-propionate toluene-4-sulfonate,
methyl 5-aminomethylisoxazole-3-propionate hydrochloride,
5-aminomethylisoxazole-3-propionic acid,
5-(1-amino-1-methylethyl)isoxazole-3-propionic acid,
5-benzylaminomethylisoxazole-3-propionic acid,
5-dimethylaminomethylisoxazole-3-propionic acid,
(−)-menthyl-3-carboxy-2-isoxazoline-5-yl-carboxylatedicyclohexylammonium salt,
cis-(3,3,5)-trimethylcyclohexyl-5-trimethylammoniomethylisoxazole-3-propionate iodide,
methyl-3-hydroxyliminomethyl-isoxazole-5-propionate,
3,5-dicarboxyl-2-isoxazoline,
5-hydroxylmethyl-isoxazole-3-propionate-sodium salt,
5-acetamidomethylisoxazole-3-propionic acid,
(−)-menthyl 5-trimethylammoniomethylisoxazole-3-propionate iodide,
(+)-menthyl 5-trimethylammoniomethylisoxazole-3-propionate iodide,
(+)-menthyl 5-(L-phenylalanylaminomethyl)isoxazole-3-propionate hydrochloride,
(−)-menthyl 5-(L-phenylalanylaminomethyl)isoxazole-3-propionate hydrochloride,
methyl 5-(L-phenylalanylaminomethyl)isoxazole-3-propionate hydrochloride,
5-guanidinomethylisoxazole-3-propionic acid,
N-(5-aminomethylisoxazol-3-yl)propionylglycine,
(+)-menthyl 5-aminomethyl-2-isoxazoline-3-propionate toluene-4-sulfonate,
(−)-menthyl 5-aminomethyl-2-isoxazoline-3-propionate toluene-4-sulfonate,
5-trimethylammoniomethylisoxazole-3-propionic acid ester,
5-aminomethylisoxazole-3-propionamide hydrochloride and
5-(L-phenylalanylaminomethyl)isoxazol-3-ylpropionylglycine trifluoroacetate.

9. A pharmaceutical composition which comprises at least one compound of the formula Ia, Ib or Ic

(Ia)

(Ib)

(Ic)

in which
R¹ is a radical of the formula IIa or IIb

(IIa)

-continued

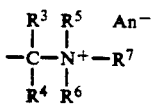  (IIb)

in which

R³ and R⁴ independently of one another are hydrogen or $C_1$-$C_4$-alkyl;

R⁵ in formula IIa is a free electron pair;

R⁵ in formula IIb is hydrogen, ($C_1$-$C_4$)-alkyl or ($C_3$-$C_6$)-cycloalkyl;

R⁶ and R⁷ independently of one another are hydrogen; $C_1$-$C_6$-alkyl; $C_3$-$C_6$-cycloalkyl; $C_6$-$C_{12}$-aryl-$C_1$-$C_4$-alkyl; carbamimidoyl; $C_1$-$C_6$-alkylcarbonyl, $C_1$-$C_4$-alkenylcarbonyl, $C_1$-$C_6$-alkloxycarbonyl, $C_6$-$C_{12}$-aryl-$C_1$-$C_4$-alkylcarbonyl, $C_6$-$C_{10}$-aryl-$C_1$-$C_4$-alkyloxycarbonyl, $C_6$-$C_{10}$-arylcarbonyl, or the radical of a naturally occurring α-amino acid or γ-aminobutyric acid which can be substituted by $C_1$-$C_6$-alkyl, hydroxyl, halogen, amino or nitro, which radical is bonded to the nitrogen of the formula II by an amide binding; or R⁵, R⁶ and R⁷ in formula IIb independently of one another are $C_1$-$C_4$-alkyl or $C_3$-$C_6$-cycloalkyl;

An⁻ is an anion radical of a physiologically acceptable salt, or an internal anionic radical when the compound is a zwitterion.

R² is a radical of the formula III

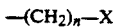  (III)

in which n is 0 or an integer from 1 to 4;

X is hydroxyl; $C_1$-$C_4$-alkyloxy; carbonyl; formyl; oxyimino; haloformyl; $C_1$-$C_{12}$-alkyloxycarbonyl; benzyloxycarbonyl, $C_3$-$C_6$-cycloalkyloxycarbonyl or said benzyloxycarbonyl or $C_3$-$C_6$-cycloalkyloxycarbonyl which is monosubstituted or polysubstituted by $C_1$-$C_6$-alkyl; or X is carbonyl which is linked by a peptide bond to a naturally occurring α-amino acid, γ-aminobutyric acid or a naturally occurring dipeptide, or X is aminocarbonyl in which amino can be mono- or disubstituted by $C_1$-$C_6$-alkyl or monosubstituted by phenyl-$C_1$-$C_6$-alkyl; and A is a C,C-single or a C,C-double bond, together with a suitable pharmaceutical excipient.

10. A pharmaceutical composition of the formula Ia or Ib as claimed in claim 9, in which R¹ is a radical of the formula IIa or IIb as claimed in claim 9, in which R³ and R⁴ independently of one another are hydrogen or $C_1$-$C_4$-alkyl;

R⁵ in formula IIa is a free electron pair;

R⁵ in formula IIb is hydrogen, ($C_1$-$C_4$)-alkyl or ($C_3$-$C_6$)-cycloalkyl;

R⁶ and R⁷ independently of one another are hydrogen; $C_1$-$C_4$-alkyl; or phenyl-$C_1$-$C_2$-alkyl; or R⁶ is hydrogen and R⁷ is a carbamimidoyl; $C_1$-$C_6$-alkylcarbonyl, $C_1$-$C_4$-alkenylcarbonyl, $C_1$-$C_6$-alkyloxycarbonyl, phenyl-$C_1$-$C_4$-alkylcarbonyl, benzyloxycarbonyl, benzoyl, or the radical of a naturally occurring α-amino acid or γ-aminobutyric acid, which can be substituted by $C_1$-$C_4$-alkyl, hydroxyl, halogen, amino or nitro, which radical is bonded to the nitrogen of the formula II by an amide binding; or R⁵, R⁶ and R⁷ in formula IIb independently of one another are $C_1$-$C_4$-alkyl or $C_3$-$C_6$-cycloalkyl;

R² is a radical of the formula III as claimed in claim 9, in which n is 0 or an integer from 1 to 3;

X is hydroxyl; $C_1$-$C_4$-alkyloxy; carboxyl; $C_1$-$C_4$-alkyloxycarbonyl; benzyloxycarbonyl, $C_3$-$C_6$-cycloalkyloxycarbonyl or said benzyloxycarbonyl or $C_3$-$C_6$-cycloalkyloxycarbonyl which is mono- or polysubstituted by $C_1$-$C_6$-alkyl; or X is carbonyl which is linked by a peptide bond to a naturally occurring α-amino acid, γ-aminobutyric acid or a naturally occurring dipeptide; or X is aminocarbonyl in which amino can be mono- or disubstituted by $C_1$-$C_4$-alkyl or monosubstituted by phenyl-$C_1$-$C_4$-alkyl; and A is a C,C-single or a C,C-double bond.

11. A pharmaceutical composition of the formula Ia as claimed in claim 9, in which R¹ is a radical of the formula II as claimed in claim 9, in which R³ and R⁴ independently of one another are hydrogen or $C_1$-$C_4$-alkyl;

R⁵ in formula IIa is a free electron pair;

R⁵ in formula IIb is hydrogen, ($C_1$-$C_4$)-alkyl or ($C_3$-$C_6$)-cycloalkyl;

R⁶ and R⁷ independently of one another are hydrogen; $C_1$-$C_4$-alkyl; or phenyl-$C_1$-$C_2$-alkyl; or R⁶ is hydrogen and R⁷ is carbamimidoyl, $C_1$-$C_6$-alkylcarbonyl or the radical of a naturally occurring α-amino acid or γ-aminobutyric acid, which radical is bonded to the nitrogen of the formula II by an amide binding; or R⁵, R⁶ and R⁷ in formula IIb are $C_1$-$C_4$-alkyl;

R² is a radical of the formula III as claimed in claim 9, in which n is 0, 1 or 2;

X is hydroxyl; $C_1$-$C_4$-alkyloxy; carboxyl; haloformyl; $C_1$-$C_4$-alkyloxycarbonyl; benzyloxycarbonyl, $C_3$-$C_6$-cycloalkoxycarbonyl or said benzyloxycarbonyl or $C_3$-$C_6$-cycloalkyloxycarbonyl which is mono- or polysubstituted by $C_1$-$C_6$-alkyl; or X is carbonyl which can be linked by a peptide bond to a naturally occurring α-amino acid or γ-aminobutyric acid; or X is aminocarbonyl in which amino is mono- or disubstituted by $C_1$-$C_4$-alkyl; and A is a C,C-single or a C,C-double bond.

12. A pharmaceutical composition of the formula Ia as claimed in claim 9, in which R¹ is a radical of the formula IIa or IIb as claimed in claim 9, in which R³ and R⁴ independently of one another are hydrogen or $C_1$-$C_4$-alkyl;

R⁵ in formula IIa is a free electron pair;

R⁵ in formula IIb is hydrogen, ($C_1$-$C_4$)-alkyl or ($C_3$-$C_6$)-cycloalkyl;

R⁶ and R⁷ independently of one another are hydrogen; $C_1$-$C_4$-alkyl; or benzyl; or R⁶ is hydrogen and R⁷ is a carbamimidoyl; $C_1$-$C_6$-alkylcarbonyl, or the radical of a naturally occurring α-amino acid, which radical is bonded to the nitrogen of the formula II by an amide binding; or R⁵, R⁶ and R⁷ in formula IIb are $C_1$-$C_4$-alkyl;

$R^2$ is a radical of the formula III as claimed in claim 9, in which n is 0, 1 or 2;

X is hydroxyl, carboxyl; $C_1$-$C_4$-alkyloxycarbonyl; benzyloxycarbonyl, cyclohexyloxycarbonyl or said benzyloxycarbonyl or cyclohexyloxycarbonyl which is mono- or polysubstituted by $C_1$-$C_6$-alkyl; or X is carbonyl which can be linked by a peptide bond to a naturally occurring α-amino acid; and A is a C,C-single or a C,C-double bond.

13. A pharmaceutical composition of the formula Ib as claimed in claim 9, in which $R^1$ is a radical of the formula IIa or IIb as claimed in claim 9, in which $R^3$ and $R^4$ are hydrogen;

$R^5$ in formula IIa is a free electron pair;

$R^5$ in formula IIb is hydrogen, ($C_1$-$C_4$)-alkyl or ($C_3$-$C_6$)-cycloalkyl;

$R^6$ and $R^7$ independently of one another are hydrogen; $C_1$-$C_4$-alkyl; or phenyl-$C_1$-$C_2$-alkyl; or $R^6$ is hydrogen and $R^7$ is $C_1$-$C_4$-acyl; $C_1$-$C_6$-alkylcarbonyl, benzoyl or the radical of a naturally occurring α-amino acid or γ-aminobutyric acid, which radical is bonded to the nitrogen of the formula II by an amide binding; or $R^5$, $R^6$ and $R^7$ in formula IIb independently of one another are $C_1$-$C_4$-alkyl or $C_3$-$C_6$-cycloalkyl;

$R^2$ is a radical of the formula III as claimed in claim 9, in which n is 0, 1 or 2;

X is carboxyl; haloformyl; $C_1$-$C_4$-alkyloxycarbonyl; benzyloxycarbonyl, $C_3$-$C_6$-cycloalkylcarbonyl or said benzyloxycarbonyl or $C_3$-$C_6$-cycloalkylcarbonyl which is mono- or polysubstituted by $C_1$-$C_6$-alkyl; or X is carbonyl which is linked by a peptide bond to a naturally occurring α-amino acid or γ-aminobutyric acid; or X is aminocarbonyl in which amino can be mono- or disubstituted by $C_1$-$C_4$-alkyl; and A is a C,C-single or a C,C-double bond.

14. A pharmaceutical composition of the formula Ib as claimed in claim 9, in which $R^1$ is a radical of the formula II as claimed in claim 9, in which $R^3$ and $R^4$ are hydrogen;

$R^5$ in formula IIa is a free electron pair;

$R^5$ in formula IIb is hydrogen, ($C_1$-$C_4$)-alkyl or ($C_3$-$C_6$)-cycloalkyl;

$R^6$ and $R^7$ independently of one another are hydrogen or $C_1$-$C_4$-alkyl; or $R^6$ is hydrogen and $R^7$ is $C_1$-$C_6$-alkylcarbonyl; or $R^5$, $R^6$ and $R^7$ in formula IIb are $C_1$-$C_4$-alkyl;

$R^2$ is a radical of the formula III as claimed in claim 24, in which n is 2 and X is carboxyl, $C_1$-$C_4$-alkyloxycarbonyl; benzyloxycarbonyl; cyclohexylcarbonyl or cyclohexylcarbonyl which is mono- or polysubstituted by $C_1$-$C_6$-alkyl; or X is carbonyl which is linked by a peptide bond to a naturally occurring α-amino acid; and A is a C,C-single or a C,C-double bond.

15. A pharmaceutical composition of the formula Ia as claimed in claim 9, in which A is a C,C-double bond.

16. A pharmaceutical composition as claimed in claim 9, wherein the compound of the formula Ia, Ib or Ic is selected from the group consisting of benzyl 5-aminomethylisoxazole-3-propionate hydrochloride, ethyl 5-aminomethylisoxazole-3-propionate hydrochloride, (+)-menthyl 5-aminomethylisoxazole-3-propionate toluene-4-sulfonate, (−)-menthyl 5-aminomethylisoxazole-3-propionate toluene-4-sulfonate, cis-(3,3,5)trimethylcyclohexyl 5-aminomethylisoxazole-3-propionate toluene-4-sulfonate, methyl 5-aminomethylisoxazole-3-propionate hydrochloride, 5-aminomethylisoxazole-3-propionic acid, 5-(1-amino-1-methylethyl)isoxazole-3-propionic acid, 5-benzylaminomethylisoxazole-3-propionic acid, 5-dimethylaminomethylisoxazole-3-propionic acid, 5-acetamidomethylisoxazole-3-propionic acid, (−)-menthyl 5-trimethylammoniomethylisoxazole-3-propionate iodide, (−)-menthyl-3-carboxy-2isoxazoline-5-yl-carboxylatedicyclohexylammonium salt, cis-(3,3,5)-trimethylcyclohexyl-5-trimethylammoniomethylisoxazole-3-propionate iodide, methyl-3-hydroxyliminomethyl-isoxazole-5-propionate, 3,5-dicarboxyl-2-isoxazoline, 5-hydroxylmethyl-isoxazole-3-propionate-sodium salt, (+)-menthyl 5-trimethylammoniomethylisoxazole-3-propionate iodide, (+)-menthyl 5-(L-phenylalanylaminomethyl)isoxazole-3-propionate hydrochloride, (−)-menthyl 5-(L-phenylalanylaminomethyl)isoxazole-3-propionate hydrochloride, methyl 5-(L-phenylalanylaminomethyl)isoxazole-3-propionate hydrochloride, 5-guanidinomethylisoxazole-3-propionic acid, N-(5-aminomethylisoxazol-3-yl)propionylglycine, (+)-menthyl 5-aminomethyl-2-isoxazoline-3-propionate toluene-4-sulfonate, (−)-menthyl 5-aminomethyl-2-isoxazoline-3-propionate toluene-4-sulfonate, 5-trimethylammoniomethylisoxazole-3-propionic acid ester, 5-aminomethylisoxazole-3-propionamide hydrochloride and 5-(L-phenylalanylamino)methylisoxazol-3-ylpropionylglycine trifluoroacetate.

17. A pharmaceutical as claimed in claim 9, for the prophylaxis and/or treatment of pathological neurodegenerative disorders.

18. A method for the prophylactic and/or therapeutic treatment of pathological neurodegenerative disorders of the human and animal body due to hypoxia and/or ischemia which comprises administering an effective amount of a pharmaceutical composition as claimed in claim 9.

19. A method for the prophylactic and/or therapeutic treatment of pathological neurodegenerative disorders of the human and animal body due to hypoxia and/or ischemia which comprises administering an effective amount of a compound of the formula Ia, Ib or Ic as claimed in claim 1 or of a physiologically acceptable salt thereof.

* * * * *